US011613578B2

(12) United States Patent
Kim et al.

(10) Patent No.: US 11,613,578 B2
(45) Date of Patent: Mar. 28, 2023

(54) ANTIBODY BINDING TO FCRN FOR TREATING AUTOIMMUNE DISEASES

(71) Applicant: HANALL BIOPHARMA CO., LTD., Daejeon (KR)

(72) Inventors: Sung Wuk Kim, Gyeonggi-do (KR); Seung Kook Park, Seoul (KR); Jae Kap Jeong, Daejeon (KR); Hyea Kyung Ahn, Gyeonggi-do (KR); Min Sun Kim, Gyeonggi-do (KR); Eun Sun Kim, Seoul (KR); Hae-Young Yong, Gyeonggi-do (KR); Dongok Shin, Gyeonggi-do (KR); Yeon Jung Song, Gyeonggi-do (KR); Tae Hyoung Yoo, Gyeonggi-do (KR)

(73) Assignee: HANALL BIOPHARMA CO., LTD., Daejeon (KR)

( * ) Notice: Subject to any disclaimer, the term of this patent is extended or adjusted under 35 U.S.C. 154(b) by 437 days.

(21) Appl. No.: 16/710,318

(22) Filed: Dec. 11, 2019

(65) Prior Publication Data
US 2020/0109201 A1   Apr. 9, 2020

Related U.S. Application Data

(63) Continuation of application No. 15/301,948, filed as application No. PCT/KR2015/004424 on Apr. 30, 2015, now Pat. No. 10,544,226.

(60) Provisional application No. 61/986,742, filed on Apr. 30, 2014.

(51) Int. Cl.
| | |
|---|---|
| C07K 16/00 | (2006.01) |
| C12P 21/08 | (2006.01) |
| C07H 21/02 | (2006.01) |
| C07H 21/04 | (2006.01) |
| C12P 21/06 | (2006.01) |
| C12P 21/04 | (2006.01) |
| C12N 5/02 | (2006.01) |
| C12N 5/16 | (2006.01) |
| C12N 1/20 | (2006.01) |
| A61K 39/395 | (2006.01) |
| A61K 39/40 | (2006.01) |
| C07K 16/28 | (2006.01) |
| G01N 33/566 | (2006.01) |
| G01N 33/68 | (2006.01) |
| G01N 33/564 | (2006.01) |
| C07K 1/00 | (2006.01) |
| A61K 39/00 | (2006.01) |

(52) U.S. Cl.
CPC ......... *C07K 16/283* (2013.01); *G01N 33/564* (2013.01); *G01N 33/566* (2013.01); *G01N 33/6854* (2013.01); *A61K 2039/505* (2013.01); *C07K 2317/21* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01); *G01N 2333/70535* (2013.01)

(58) Field of Classification Search
None
See application file for complete search history.

(56) References Cited

U.S. PATENT DOCUMENTS

| | | |
|---|---|---|
| 5,714,350 A | 2/1998 | Co et al. |
| 2007/0092507 A1 | 4/2007 | Balthasar et al. |
| 2009/0098134 A1 | 4/2009 | Buelow |
| 2010/0212035 A1 | 8/2010 | Buelow |

FOREIGN PATENT DOCUMENTS

| | | |
|---|---|---|
| KR | 10-2013-0071961 A | 7/2013 |
| WO | WO 2005/013912 A2 | 2/2005 |
| WO | WO 2006/118772 A2 | 11/2006 |
| WO | WO 2007/087289 A2 | 8/2007 |
| WO | WO 2009/131702 A2 | 10/2009 |
| WO | WO 2012/167039 A1 | 12/2012 |
| WO | WO 2014/019727 A1 | 2/2014 |
| WO | WO 2014/177460 A1 | 11/2014 |
| WO | WO 2014/204280 A1 | 12/2014 |

OTHER PUBLICATIONS

Christianson, G. et al., (Mar. 2012) "Monoclonal antibodies directed against human FcRn and their applications", mAbs., 4(2):208-216.
European Patent Application No. 15785500.8, by Hanall Biopharma Co., Ltd.: Extended European Search Report, including Supplementary Search Report and Opinion, dated Jan. 30, 2018 (21 pages).
Li, N. et al., (Dec. 2005) "Complete FcRn Dependence for Intravenous Ig Therapy in Autoimmuno Skin Blistering Diseases", *The Journal of Clinical Investigation*, 115(12):3440-3450.
Lonberg, N. (Aug. 2008) "Fully human antibodies from transgenic mouse and phage display platforms", *Current Opinion in Immunology*, 20:450-459.
Menoret, S. et al., (2010) "Characterization of Immunoglobulin Heavy Chain Knockout Rats", *European Journal of Immunology*, 40:2932-2941.

(Continued)

*Primary Examiner* — Chun W Dahle
(74) *Attorney, Agent, or Firm* — Cooley LLP

(57) ABSTRACT

The present disclosure relates to an isolated anti-FcRn antibody, which is an antibody binding to FcRn (stands for neonatal Fc receptor, also called FcRP, FcRB or Brambell receptor) that is a receptor with a high affinity for IgG or a fragment thereof, a method of preparing thereof, a composition for treating autoimmune disease, which comprises the antibody, and a method of treating and diagnosing autoimmune diseases using the antibody. The FcRn-specific antibody according to the present disclosure binds to FcRn non-competitively with IgG to reduce serum pathogenic auto-antibody levels, and thus can be used for the treatment of autoimmune diseases.

23 Claims, 15 Drawing Sheets
Specification includes a Sequence Listing.

(56) References Cited

OTHER PUBLICATIONS

Odom et al., (2007) "Tissue-specific transcriptional regulation has diverged significantly between human and mouse", *Nature Genetics*, 39(6):730-732.

Osborn, M.J. et al., (Feb. 2013) "High-Affinity IgG Antibodies Develop Naturally in Ig-Knockout Rats Carrying Germline Human IgH/Igκ/Igλ Loci Bearing the Rat CH Region", *The Journal of Immunology*, 190:1481-1490.

Praetor, A. et al., (Jun. 2002) "B2-microglobulin is important for cell surface expression and pH-dependent IgG binding of human FcRn", *Journal of Cell Science*, 115:2389-2397.

Rath, T. et al., (Sep. 2012) "The Immunologic Functions of the Neonatal Fc Receptor for IgG", *Journal of Clinical Immunology: Author Manuscript*, (Supplement 1) 33:S9-S17.

Roopenian, D. et al., (Apr. 2003) "The MHC Class I-Like IgG Receptor Controls Perinatal IgG Transport, IgG Homeostasis and Fate of IgG-Fc-Coupled Drugs", The Journal of Immunology, 170:3528-3533.

Schwab, I. et al., (Feb. 2013) "Intravenous immunoglobulin therapy: how does IgG modulate the immune system?", Nature Reviews: *Immunology*, 13:176-189.

Vitetta et al., (2006) "Considering Therapeutic Antibodies", Science, 313:308-309.

Dondelinger et al., (2018) "Understanding the Significance and Implications of Antibody Numbering and Antigen-Binding Surface/Residue Definition", Frontiers in Immunology, 9:2278 (15 pages).

European Patent Application No. 15785500.8, by Hanall Biopharma Co., Ltd.: Examination Report, dated Jul. 9, 2020 (5 pages).

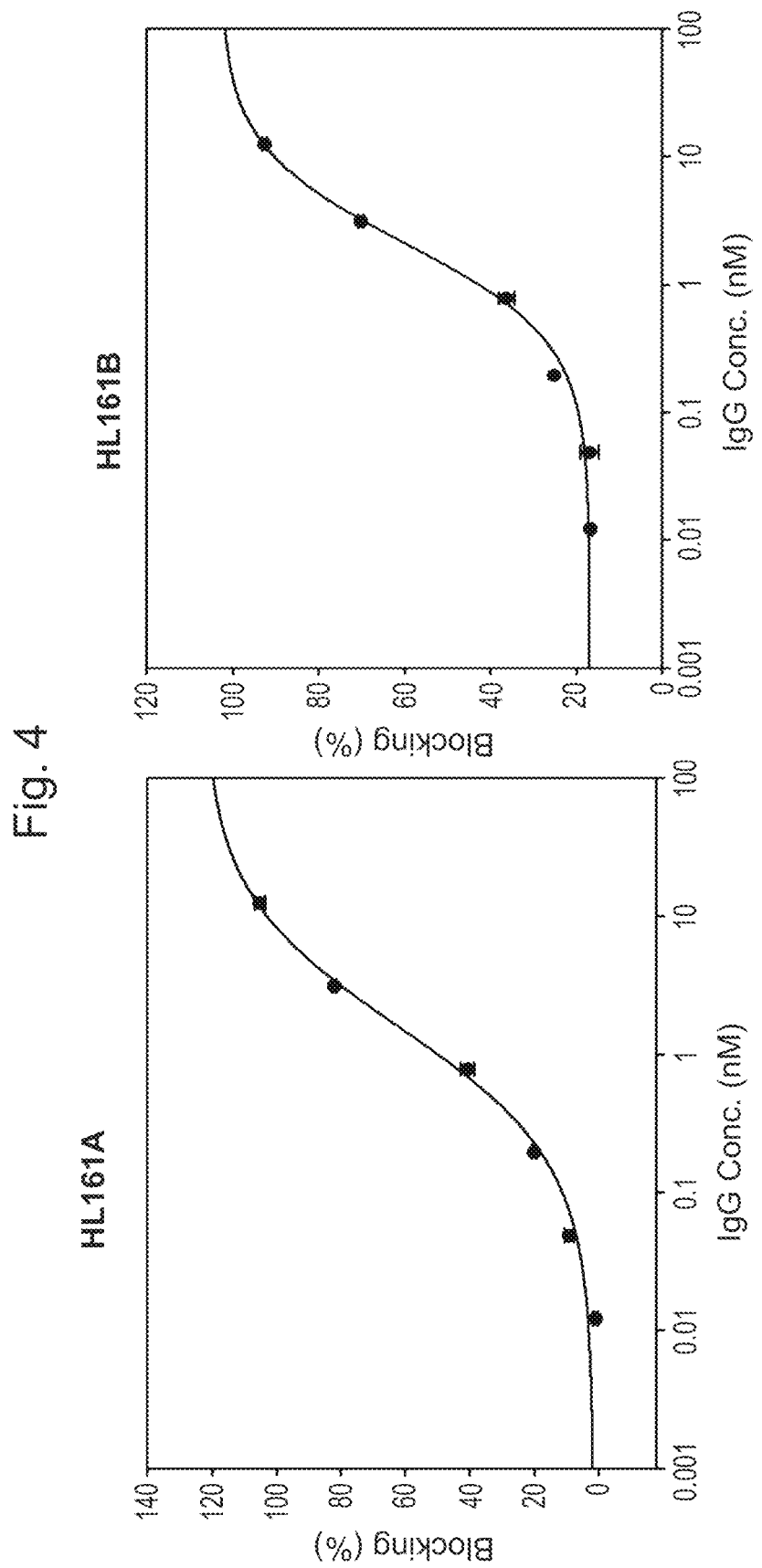

HL161A

HL161B

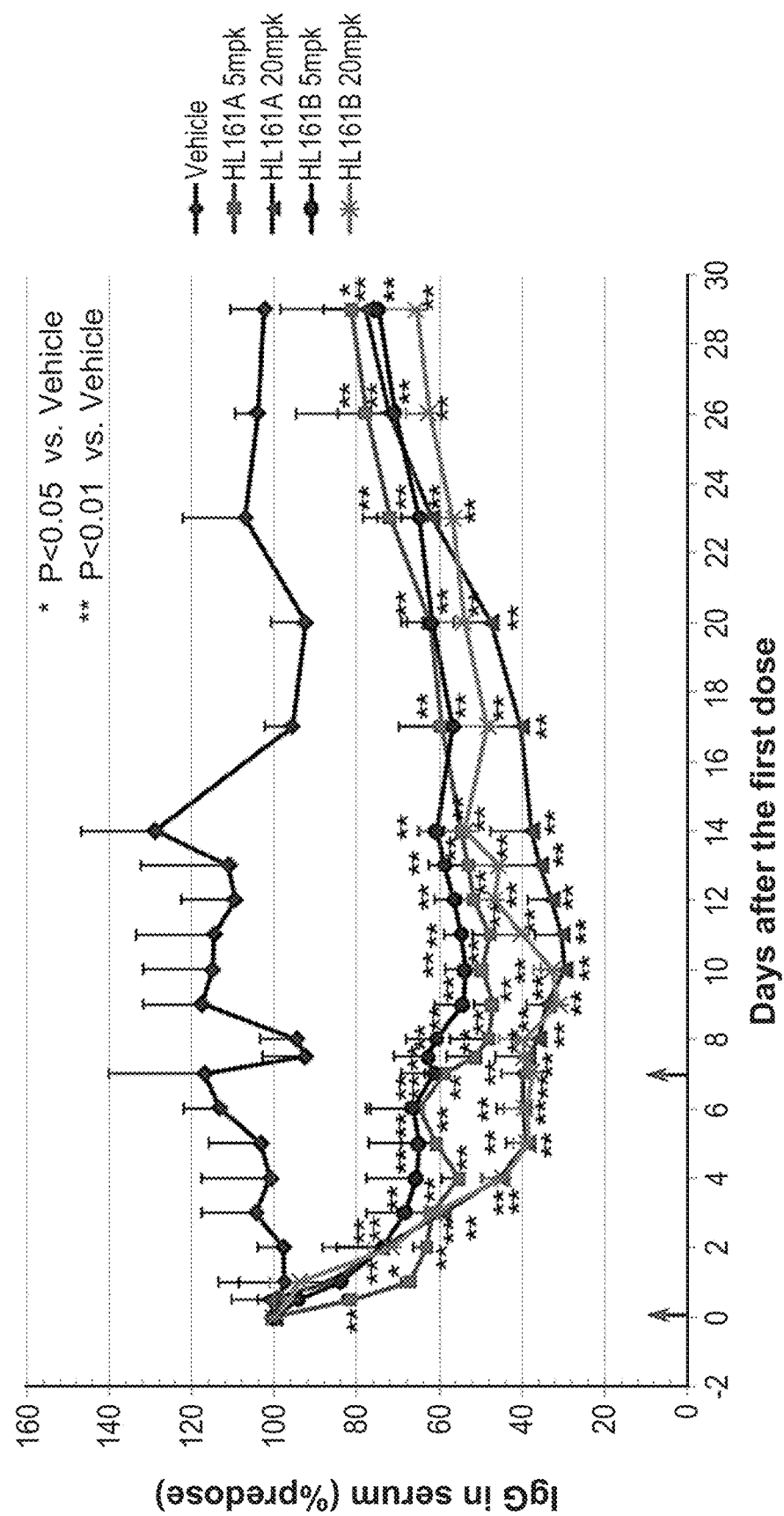

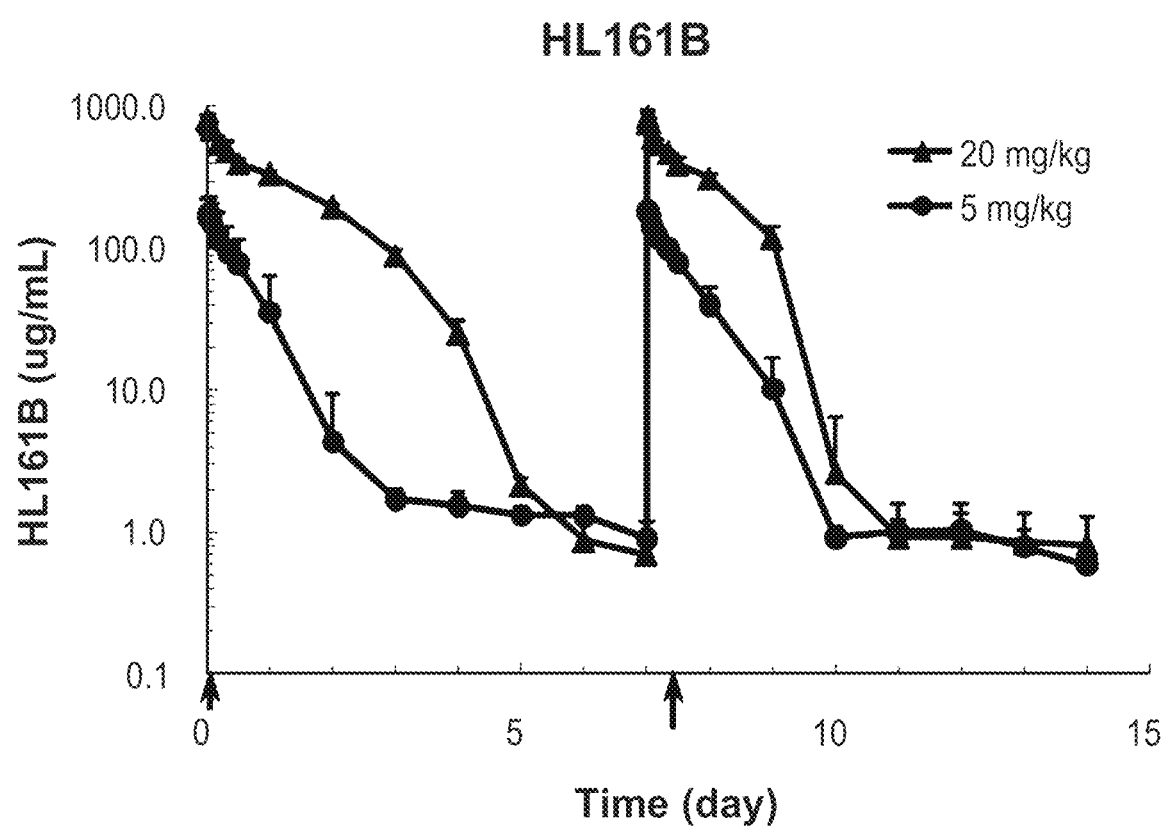

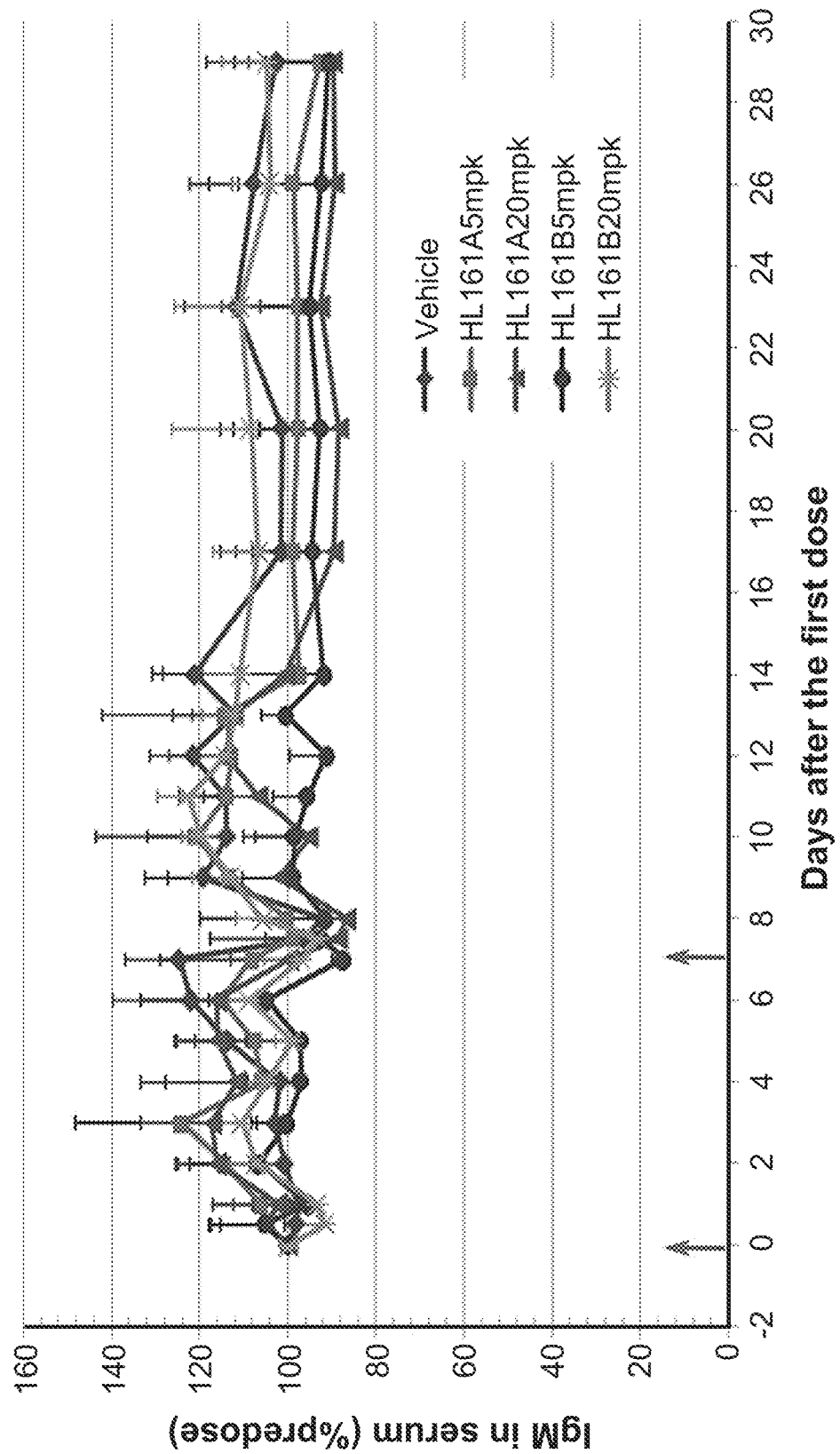

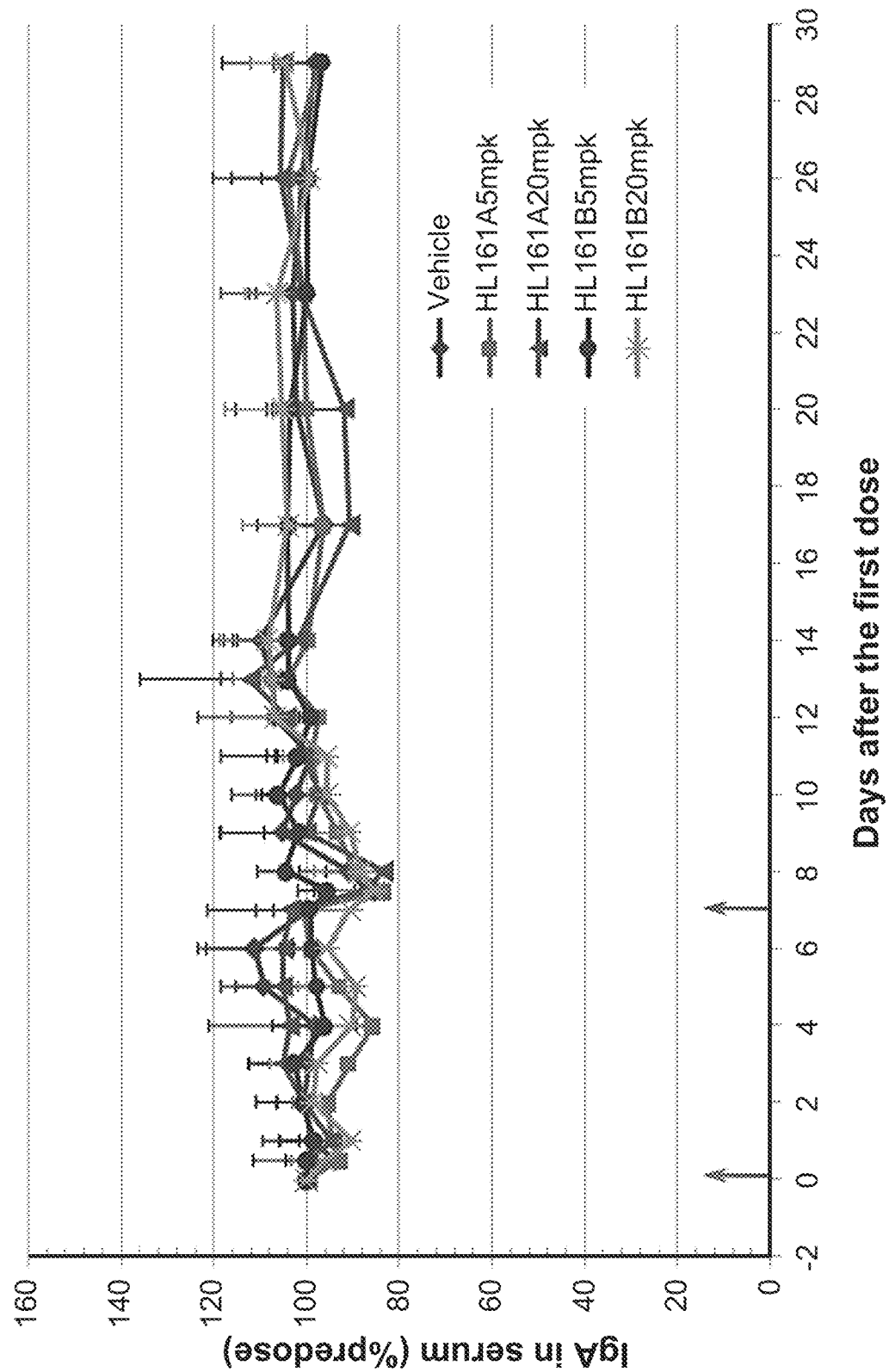

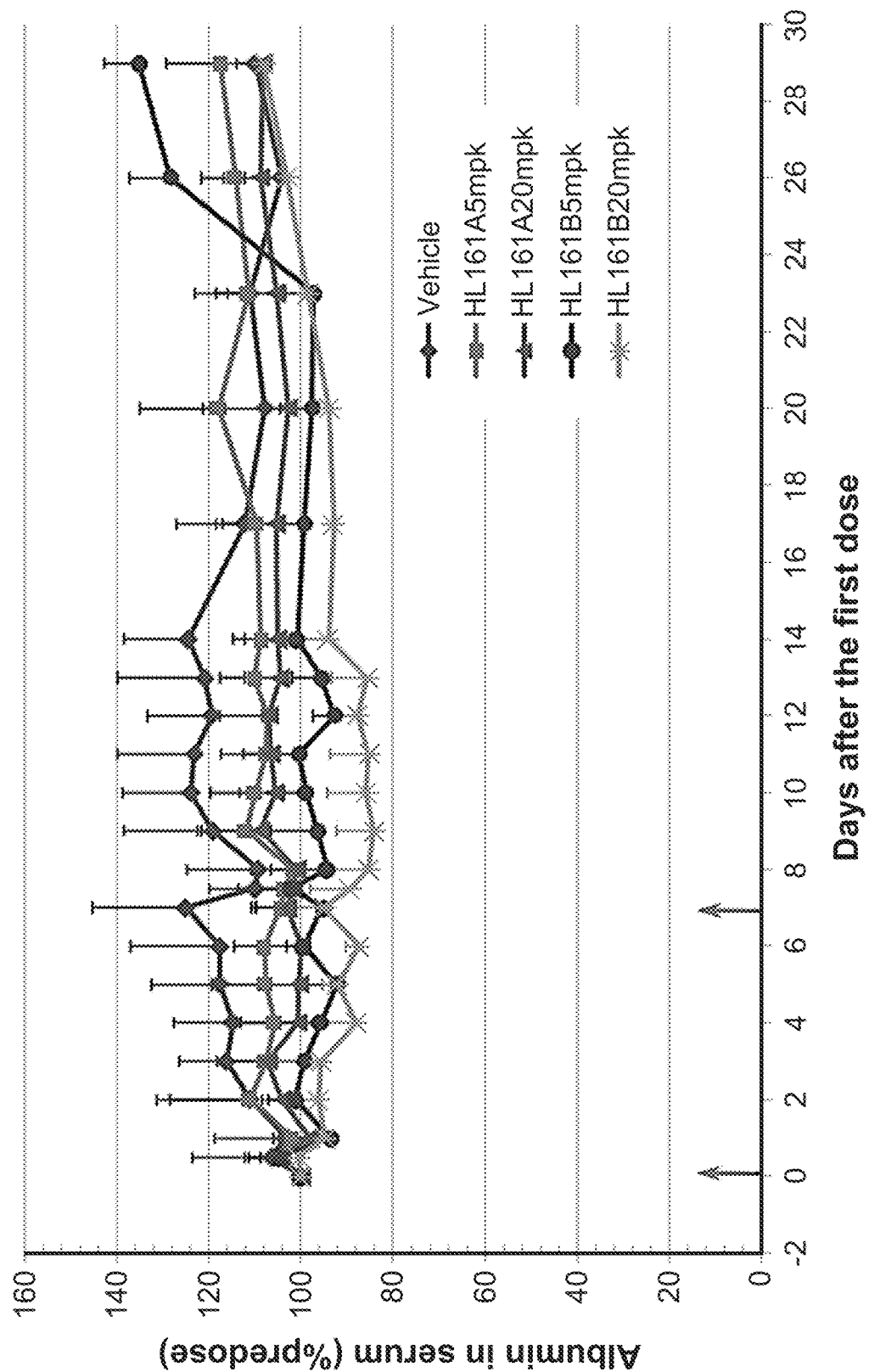

ANTIBODY BINDING TO FCRN FOR TREATING AUTOIMMUNE DISEASES

CROSS-REFERENCE TO RELATED APPLICATIONS

This application is continuation of U.S. patent application Ser. No. 15/301,948, filed Oct. 4, 2016, which is a U.S. national phase application under the provisions of 35 U.S.C. 371 of International Patent Application No. PCT/KR15/04424, filed Apr. 30, 2015, which claims priority to U.S. Provisional Patent Application No. 61/986,742, filed Apr. 30, 2014, all of which are incorporated herein by reference in their entireties, for all purposes.

SEQUENCE LISTING

This application contains a Sequence Listing which has been submitted electronically in ASCII format and is hereby incorporated by reference in its entirety. The ASCII copy is named "340SeqIDListing_ST25.txt" and is 22.01 kilobytes in size.

TECHNICAL FIELD

The present disclosure relates to an isolated anti-FcRn antibody, which is an antibody binding to FcRn (stands for neonatal Fc receptor, also called FcRP, FcRB or Brambell receptor) that is a receptor with a high affinity for IgG or a fragment thereof, a method of preparing thereof, a composition for treating autoimmune disease, which comprises the antibody, and a method of treating and diagnosing autoimmune diseases using the antibody. The FcRn-specific antibody according to the present disclosure binds to FcRn non competitively with IgG to reduce serum pathogenic autoantibody levels, and thus can be used for the treatment of autoimmune diseases.

BACKGROUND ART

Antibodies are immunological proteins that bind to a specific antigen. In most animals, including humans and mice, antibodies are constructed from paired heavy and light polypeptide chains and each chain is made up of two distinct regions, referred to as the variable and constant regions. The light and heavy chain variable regions show significant sequence diversity between antibodies, and are responsible for binding the target antigen. The constant regions show less sequence diversity, and are responsible for binding a number of natural proteins to elicit important biochemical events.

Under normal conditions, the half-life of most IgG excluding IgG3 isotype in serum is about 22-23 days in humans, which is a prolonged period relative to the serum half-life of other plasma proteins. With respect to this prolonged serum half-life of IgG, IgG that entered cells by endocytosis can strongly bind to neonatal Fc receptor (FcRn, a kind of Fc gamma receptor) in endosomes at a pH of 6.0 to avoid the degradative lysosomal pathway. When the IgG-FcRn complex cycles to the plasma membrane, IgG dissociates rapidly from FcRn in the bloodstream at slightly basic pH (~7.4). By this receptor-mediated recycling mechanism, FcRn effectively rescues the IgG from degradation in lysosomes, thereby prolonging the half-life of IgG (Roopenian et al, J. Immunol. 170:3528, 2003).

FcRn was identified in the neonatal rat out, where it functions to mediate the absorption of IgG antibody from the mother's milk and facilitates its transport to the circulatory system. FcRn has also been isolated from human placenta, where it mediates absorption and transport of maternal IgG to the fetal circulation. In adults, FcRn is expressed in a number of tissues, including epithelial tissues of the lung, intestine, kidney, as well as nasal, vaginal, and biliary tree surfaces.

FcRn is a non-covalent heterodimer that typically resides in the endosomes of endothelial and epithelial cells. FcRn a membrane bound receptor having three heavy chain alpha domains ($\alpha$1, $\alpha$2 and $\alpha$3) and a single soluble light chain $\beta$2-microglobulin ($\beta$2m) domain. Structurally, it belongs to a family of major histocompatibility complex class 1 molecules that have $\beta$2m as a common light chain. The FcRn chain has a molecular weight of about 46 kD and is composed of an ectodomain containing the $\alpha$1, $\alpha$2, and $\alpha$3 heavy chain domains and a $\beta$2m light chain domain and having a single sugar chain, a single-pass transmembrane, and a relatively short cytoplasmic tail.

In order to study the contributions of FcRn to IgG homeostasis, mice have been engineered so that at least part of the genes encoding $\beta$2m and FcRn heavy chains have been "knocked out" so that these proteins are not expressed. In these mice, the serum half-life and concentrations of IgG were dramatically reduced, suggesting an FcRn-dependent mechanism for IgG homeostasis. It has also been suggested that anti-human FcRn antibodies may be generated in these FcRn knockout mice and that these antibodies may prevent the binding of IgG to FcRn. The inhibition of IgG binding to FcRn negatively alters IgG serum half-life by preventing IgG recycling, so that autoimmune diseases caused by auto-antibodies can be treated. This possibility was shown in a mouse model of autoimmune cutaneous bullous diseases (Li et al. J. Clin. Invest. 115:3440, 2005). Accordingly, agents that block or antagonize the binding of IgG to FcRn may be used in a method for treating or preventing autoimmune and inflammatory diseases, which are mediated by IgG.

"Autoimmune diseases" cover diseases that occur when the body's immune system attacks its own normal tissues, organs or other in vivo components due to immune system abnormalities whose cause cannot be found. These autoimmune diseases are systemic diseases that can occur in almost all parts of the body, including the nervous system, the gastrointestinal system, the endocrine system, the skin, the skeletal system, and the vascular tissue. It is known that autoimmune diseases affect about 5-8% of the world population, but the reported prevalence of autoimmune diseases is lower than the actual level due to limitations in the understanding of autoimmune diseases and a method for diagnosing these diseases.

The causes of autoimmune diseases have been studied for a long period of time in terms of genetic, environmental and immunological factors, but have not yet been clearly identified. Many recent studies revealed that a number of autoimmune diseases are caused by IgG-type autoantibodies. In fact, the relation between the presence or absence of disease-specific autoantibodies and the treatment of autoimmune diseases has been widely identified from studies on the disease and the treatment of autoimmune diseases. Thus, the presence of disease-specific autoantibodies and the pathological role thereof in a large number of autoimmune diseases have been identified, and when the autoantibodies of interest are removed from blood, an effect of quickly treating diseases can be obtained.

Autoimmune diseases and autoimmune diseases are mediated by pathogenic antibodies, and typical examples thereof include immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa sclerosis, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, lupus, idiopathic Thrombocytopenic Purpura (ITP), lupus nephritis or membranous nephropathy, or the like.

For example, it is known that, in case of myasthenia gravis (MG), acetylcholine receptor (AChR) located at the neuromuscular junction voluntary muscles is destroyed or blocked by autoantibodies against the receptor to impair the function of voluntary muscles. Also, it is known that when such autoantibodies are reduced, the function of muscles is restored.

As to the case of ITP, ITP is a disease caused by the destruction of peripheral platelets due to the generation of auto-antibodies that bind to a specific platelet membrane glycoprotein. Anti-platelet antibodies opsonize platelets and result in rapid platelet destruction by reticular cells (e.g., macrophages).

In general, attempts to treat ITP include suppressing the immune system, and consequently causing an increase in platelet levels. ITP affects women more frequently than men, and is more common in children than adults. The incidence is 1 out of 10,000 people. Chronic ITP is one of the major blood disorders in both adults and children. It is a source of significant hospitalization and treatment cost at specialized hematological departments in the US and around the world. Each year there are approximately 20,000 new cases in the US, and the cost for ITP care and special therapy is extremely high. Most children with ITP have a very low platelet count that causes sudden bleeding, with typical symptoms including bruises, small red dots on the skin, nosebleeds and bleeding gums. Although children can sometimes recover with no treatment, many doctors recommend careful observation and mitigation of bleeding and treatment with intravenous infusions of gamma globulin.

It is known that the important pathogenesis of Lupus nephritis, a kind of autoimmune disease, is that an increased immune complex, which could be occurred due to the inappropriate overproduction of auto-antibodies such as anti-nuclear antibodies, is accumulated in the systemic organs to cause inflammatory responses. About 40-70% of Lupus patients have renal involvement, and about 30% of the patients develop Lupus nephritis, which is known as a bad prognostic factor in Lupus patients. Although methods of treating Lupus nephritis using immunosuppressive agents have been attempted, it was reported that remission was not induced in about 22% of Lupus nephritis patients even when immunosuppressive agents were used. Also, it was reported that, even when remission was induced, 10-65% of patients relapsed into Lupus nephritis when the use of immunosuppressive agents was reduced. Ultimately, 5-10% of patients with serious Lupus nephritis (WHO class III and IV) die after 10 years, and 5-15% of the patients lead to end-stage renal stage. Thus, appropriate treatment of Lupus nephritis has not yet been reported.

Thus, the use of antibodies having a new mechanism that treat autoimmune diseases by clearing pathogenic autoantibodies is expected to have therapeutic effects against pathogenic IgG-mediated autoimmune diseases such as pemphigus vulgaris, neuromyelitis optica and myasthenia gravis, as well as immune complex-mediated glomerular diseases such as Lupus nephritis or membraneous nephropathy.

Methods of treating autoimmune diseases by intravenous administration of IgG (IVIG) in large amounts have been widely used (Arnson Autoimmunity 42:553, 2009). IVIG effects are explained by various mechanisms, but are also explained by the mechanism that increases the clearance of pathogenic antibodies by competition with endogenous IgG for FcRn. Intravenous administration of human immunoglobulin (IVIG) in large amounts has been shown to increase platelet counts in children afflicted with immune ITP, and IVIG has shown to be beneficial as a treatment for several other autoimmune conditions. Many studies have investigated the mechanisms by which IVIG achieves effects in the treatment of autoimmune diseases. With regard to ITP, early investigations led to the conclusion that IVIG effects are mainly due to blockade of the Fc receptors responsible for phagocytosis of antibody-opsonized platelets. Subsequent studies showed that Fc-depleted IVIG preparations provided increases in platelet counts in some patients with ITP, and recently it was reported that IVIG effects are due to stimulation of FcγRIIb expression on macrophage cells, leading to inhibition of platelet phagocytosis.

However, such IVIG treatments have substantial side effects and are very costly to administer. Further, other therapies used for the treatment of autoimmune/autoimmune conditions other than IVIG include polyclonal anti-D immunoglobulin, corticosteroids, immuno-suppressants (including chemotherapeutics), cytokines, plasmapheresis, extracorporeal antibody adsorption (e.g., using Prosorba columns), surgical interventions such as splenectomy, and others. However, like IVIG, these therapies are also complicated by incomplete efficacy and high cost. Also, very high doses of IVIG are required to produce substantial increases in the clearance of pathogenic antibody due to the putative mechanism of IVIG inhibition of FcRn binding with pathogenic antibody (i.e., competitive inhibition) and due to the fact that IgG shows very low affinity for FcRn at physiologic pH (i.e., pH 7.2-7.4), and the typical clinical dose of IVIG is about 2 g/kg.

The use of an inhibitor that competitively inhibits the binding of IgG to FcRn to treat autoimmune diseases is a promising therapeutic method. However, owing to the high affinity of endogenous IgG for FcRn and to the high concentrations of endogenous IgG in blood, it is likely that competitive inhibition of FcRn would require very high doses, and thus have the same limitations similar to those of the current IVIG treatment.

Accordingly, although the anti-FcRn antibody is disclosed in WO2006/118772, WO2007/087289, WO2009/131702, WO2012/167039, there is an urgent need for the development of an improved human antibody that has a high affinity for FcRn, and thus can remove pathogenic antibody even at low doses and reduce immunogenicity.

DISCLOSURE OF INVENTION

Technical Problem

The present inventors have made extensive efforts to solve the above-described problems and to provide a medicament for effectively and fundamentally treating autoimmune disease including ITP, and finally provide an antibody that has a high affinity for FcRn or a fragment thereof and a method of preparing the same. The antibody binding to FcRn or a fragment thereof, binds specifically to the FcRn chain in a pH-independent, manner and interferes non-competitively with the binding of Fc of antibody to FcRn, to treat autoimmune disease by reducing autologous antibody in vivo, which could be a cause of autoimmune disease.

It is an object of the present disclosure to provide a pharmaceutical composition for treating autoimmune diseases, comprising the antibody binding to FcRn, wherein the autoimmune disease is immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa acquisita, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, lupus, idiopathic thrombocytopenic purpura, lupus nephritis or membranous nephropathy, or the like.

Technical Solution

To achieve the above objects, the present disclosure provides an isolated anti-FcRn antibody comprising:

CDR1 comprising one or more amino acid sequence selected from the group consisting of SEQ ID Nos: 21, 24, 27, 30, 33, 36, 39 and 42;

CDR2 comprising one or more amino acid sequence selected from the group consisting of SEQ ID Nos: 22, 25, 28, 31, 34, 37, 40 and 43; and CDR3 comprising one or more amino acid sequence selected from the group consisting of SEQ ID Nos: 23, 26, 29, 32, 35, 38, 41 and 44, or a fragment thereof.

Further, the present disclosure provides an isolated anti-FcRn antibody or a fragment thereof comprising:

CDR1 comprising amino acid sequence, which has at least 90% homology with one or more amino acid sequence selected from the group consisting of SEQ ID No: 21, 24, 27, 30, 33, 36, 39 and 42;

CDR2 comprising amino acid sequence, which has at least 90% homology with one or more amino acid sequence selected from the group consisting of SEQ ID No: 22, 25, 28, 31, 34, 37, 40 and 43; and CDR3 comprising amino acid sequence, which has at least 90% homology with one or more amino acid sequence selected from the group consisting of SEQ ID No: 23, 26, 29, 32, 35, 38, 41 and 44.

Further, the present disclosure provides an isolated anti-FcRn antibody comprising one or more heavy chain variable regions and light chain variable regions comprising one or more amino acid sequences selected from the group consisting of amino acid sequences of SEQ ID Nos: 2, 4, 6, 8, 10, 12, 14, 16, 18 and 20.

Further, the present disclosure provides an isolated anti-FcRn antibody comprising one or more heavy chain variable regions and light chain variable regions comprising amino acid sequence, which has at least 90% homology with one or more amino acid sequences selected from the group consisting of amino acid sequences of SEQ ID Nos: 2, 4, 6, 8, 10, 12, 14, 16, 18 and 20.

Further, the present disclosure provides polynucleotide encoding the anti-FcRn antibody or a fragment thereof.

Further, the present disclosure provides polynucleotide encoding an anti-FcRn antibody comprising one or more sequence selected from the group consisting of SEQ ID Nos: 1, 3, 5, 7, 9 11, 13, 15, 17 and 19.

Further, the present disclosure provides polynucleotide encoding an anti-FcRn antibody comprising sequence, which has at least 90% homology with one or more sequence selected from the group consisting of SEQ ID Nos: 1, 3, 5, 7, 9, 11, 13, 15, 17 and 19.

Further, the present disclosure provides recombinant expression vector comprising the polynucleotide, host cell, which is transfected with the recombinant expression vector. The present disclosure additionally provides a method of preparing an antibody binding specifically to FcRn or a fragment thereof comprising: culturing the host cell and producing the antibody therefrom; and isolating and purifying the produced antibody to recover the anti-FcRn antibody.

Further, the present disclosure provides a pharmaceutical composition comprising the anti-FcRn antibody or a fragment thereof, and one or more pharmaceutically acceptable carrier.

Further, the present disclosure provides a method of treating a patient suffering from an autoimmune disease, comprising administering the composition to said patient.

Further, the present disclosure provides a composition comprising the antibody labelled with a detection label.

Further, the present disclosure provides a method of detecting FcRn in vivo or in vitro comprising using the anti-FcRn antibody or a fragment thereof.

Advantageous Effects

The inventive antibody or a fragment thereof specific for FcRn that is a receptor having a high affinity for IgG has high affinity and specificity, causes little or no immunogenicity-related problems, and binds to FcRn non-competitively with IgG or the like to reduce serum auto-antibody levels. By virtue of such properties, the antibody or a fragment thereof is useful for the treatment and diagnosis of autoimmune diseases.

BRIEF DESCRIPTION OF THE DRAWINGS

In FIG. 1, lane 1 represents a molecular weight (M. W.) marker, lane 2 represents 2 μg non-reduced (*NEM-treated) antibody, and lane 3 represents 2 μg reduced antibody.

FIG. 2A shows the results of analyzing the interaction between human FcRn and the HL161A antibody at pH 6.0.

FIG. 2B shows the results of analyzing the interaction between human FcRn and the HL161A antibody at pH 7.4.

FIG. 2C shows the results of analyzing the interaction between human FcRn and the HL161B antibody at pH 6.0.

FIG. 2D shows the results of analyzing the interaction between human FcRn and the HL161B antibody at pH 7.4.

FIG. 2E shows the results of analyzing the interaction between human FcRn and the HL161C antibody at pH 6.0.

FIG. 2F shows the results of analyzing the interaction between human FcRn and the HL161C antibody at pH 7.4.

FIG. 2G shows the results of analyzing the interaction between human FcRn and the HL161D antibody at pH 6.0.

FIG. 2H shows the results of analyzing the interaction between human FcRn and the HL161D antibody at pH 7.4.

FIG. 4 shows the results of analyzing the ability to block the binding of human IgG to human FcRn expressing cells at pH 6.0, and shows the results of observing whether two selected antibodies binding to cell surface human FcRn can block the binding of human IgG to human FcRn, at the cell level. A profile about the ability to block the binding of Alexa488-labelled human IgG to human FcRn was obtained by diluting each of HL161A and HL161B antibodies, confirmed to bind to human FcRn-overexpressing HEK293 cells, serially 4-fold from 200 nM.

FIGS. 6A through 6C show the results of analyzing the change in blood level or monkey IgG caused by administration of two antibodies (HL161A and HL161B) to cynomolgus monkeys having a sequence homology of 96% to human FcRn. Each of HL161A and HL161B antibodies was administered intravenously to cynomolgus monkeys at doses of 5 and 20 mg/kg once a day, and as a result, at was shown that monkey IgG decreased up to 70% compared to that at 0 hour, and decreased by about 30% up to day 29.

FIG. 6A shows the serum IgG-reducing effects of HL161A and HL161B antibodies at varying antibody concentrations.

FIG. 6B shows the serum IgG-reducing effects of HL161A and HL161B antibodies (concentration: (5 mg/kg) in monkey individuals.

FIG. 6C shows the serum IgG-reducing effects of HL161A and HL161B antibodies (concentration: (20 mg/kg) in monkey individuals.

FIGS. 7A and 7B show the results of analyzing the pharmacokinetic profiles of HL161A and HL161B in an experiment performed using cynomolgus monkeys. It was shown that HL161B had a high half-life AUC and Cmax overall compared to HL161A.

FIGS. 8A through 8C show the results of analyzing the changes in blood levels of monkey IgM, IgA and albumin caused by administration of HL161A and HL161B antibodies in an experiment performed using cynomolgus monkeys. There were slight changes in the blood levels of monkey IgM, IgA and albumin, such changes were within the normal ranges of cynomolgus monkeys, suggesting that such changes resulted from a difference between individuals rather than the influence of the test substances.

FIG. 8A shows a change in the serum IgM level of monkeys.

FIG. 8B shows a change in the serum IgA level of monkeys.

FIG. 8C shows a change in the serum albumin level of monkeys.

MODE FOR INVENTION

Figure 1:
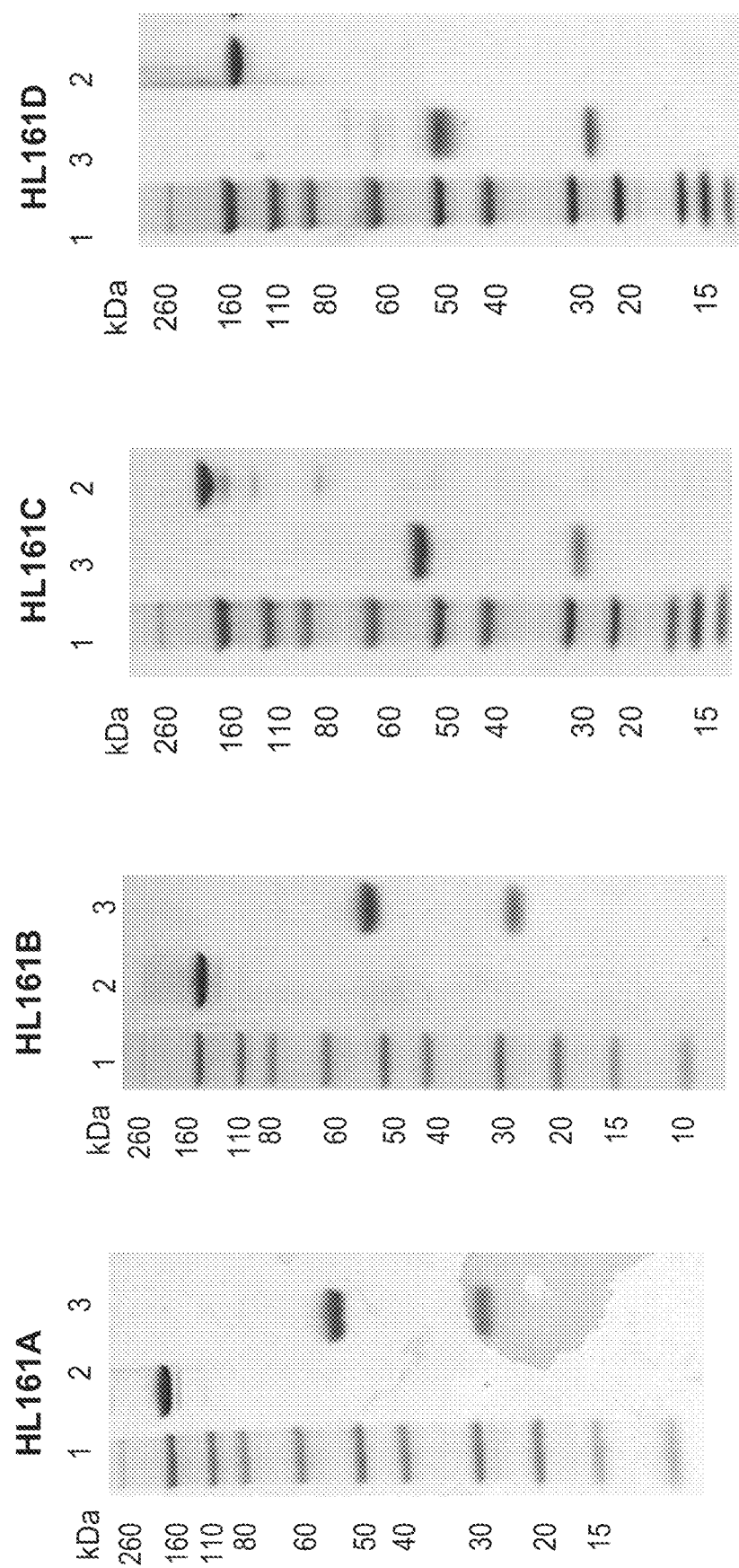
FIG. 1 shows the results of analyzing the expression of antibodies in CHO-S cells and analyzing HL161A, HL161B, HL161C and HL161D antibody proteins, obtained by protein. A purification, on SDS-PAGE gel under a reduced or non-reduced condition. It was shown that, under a non-reduced condition, each of the HL161 antibodies had a whole human IgG1 type structure having a size of about 160 kDa, and under a reduced condition, the heavy chain had a size of about 55 kDa, and the light chain had a size of about 25 kDa, suggesting that the antibody was composed of typical antibody subunits.
Figure 2A:
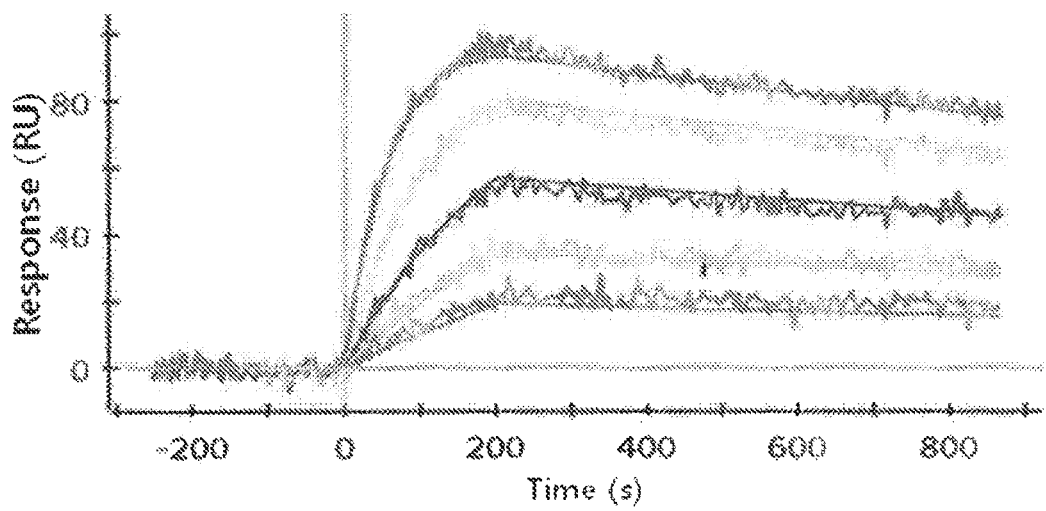
FIGS. 2A through 2H show the results of analysis performed using a SPR system in order to determine the kinetic dissociation (KD) of four kinds of anti-FcRn antibodies (HL161A, HL161B, HL161C and HL161D) that bind to FcRn. The results in FIGS. 2A through 2H were obtained by analyzing the interaction between human FcRn and the HL161A, HL161B, HL161C or HL161D antibody at pH 6.0 and pH 7.4 using a Proteon GIG chip and a Proteon XPR36 (Bio-Rad) system.
Figure 2B:
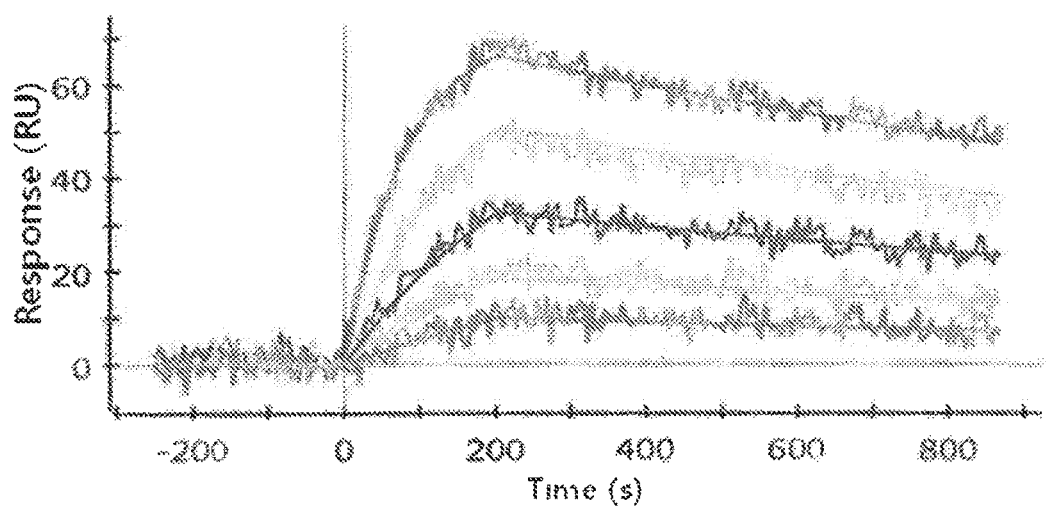
Figure 2C:
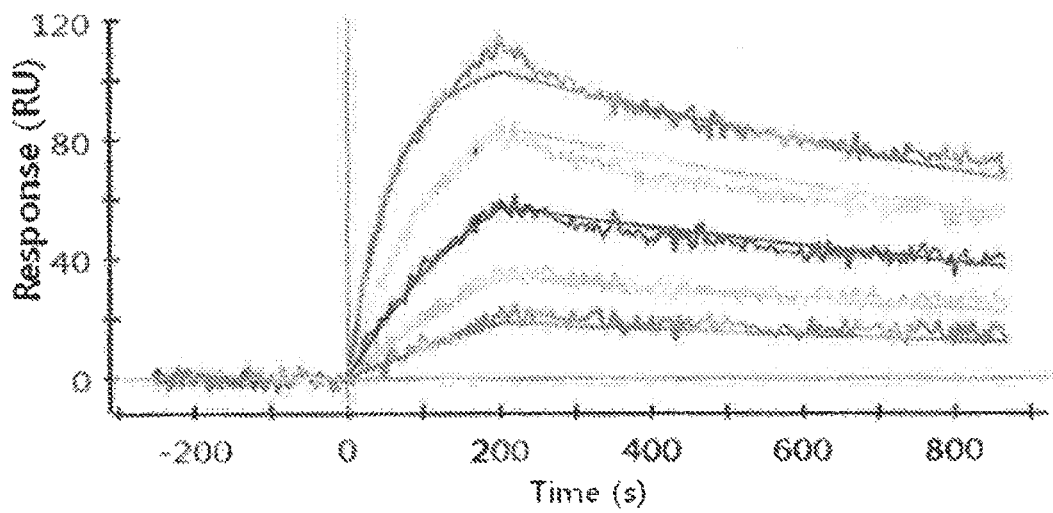
Figure 2D:
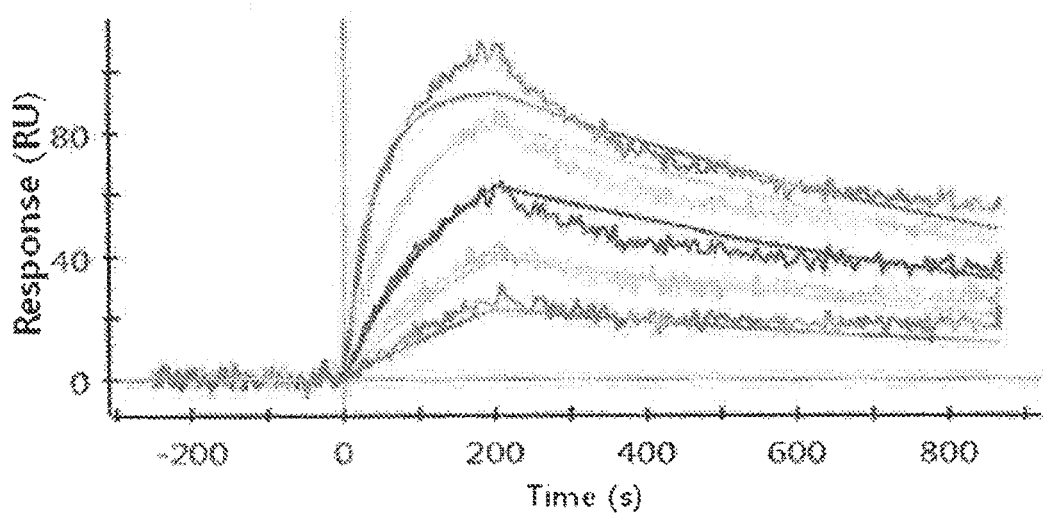
Figure 2E:
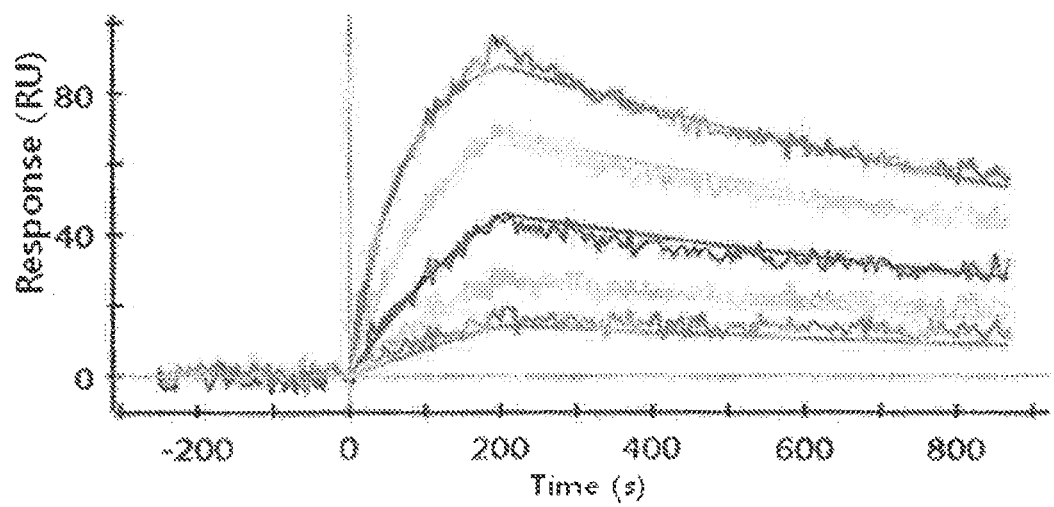
Figure 2F:
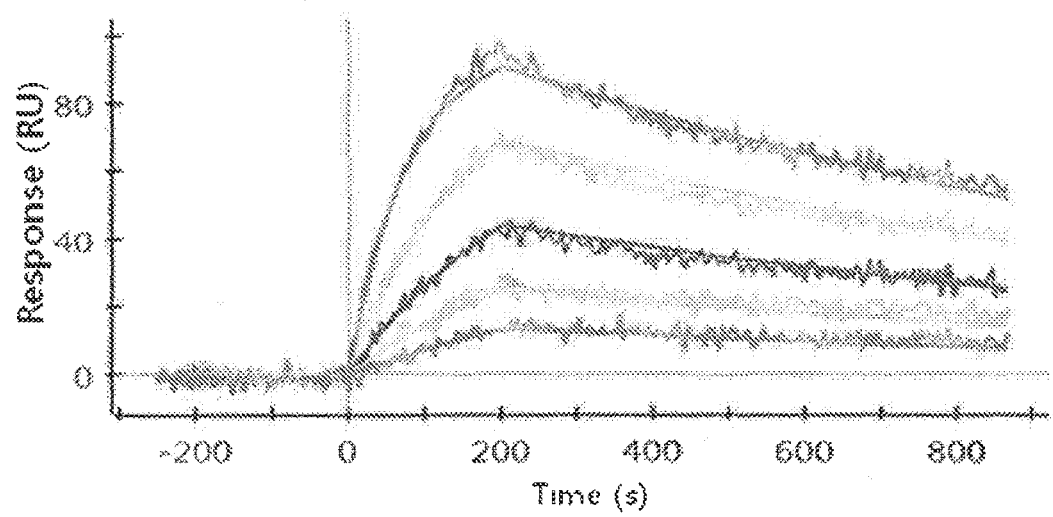
Figure 2G:
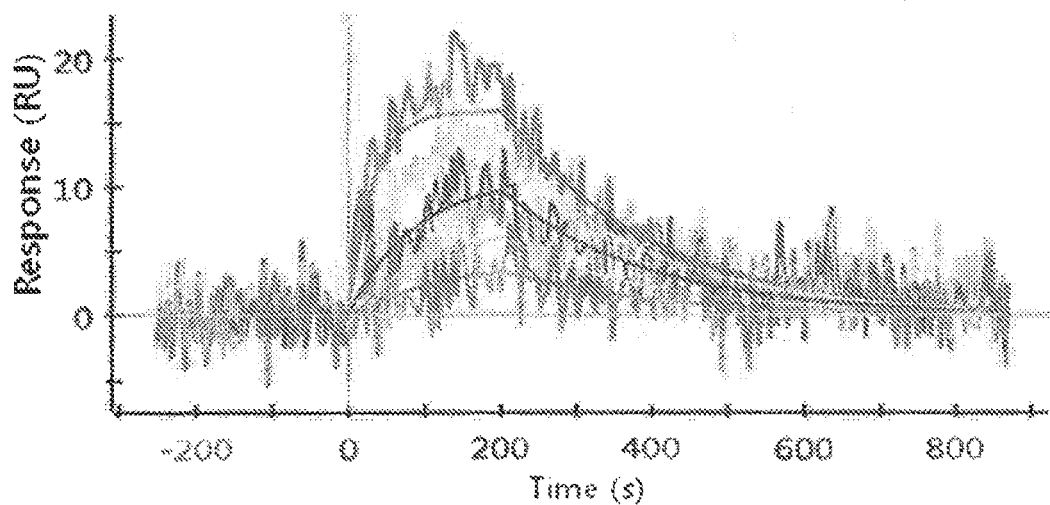
Figure 2H:
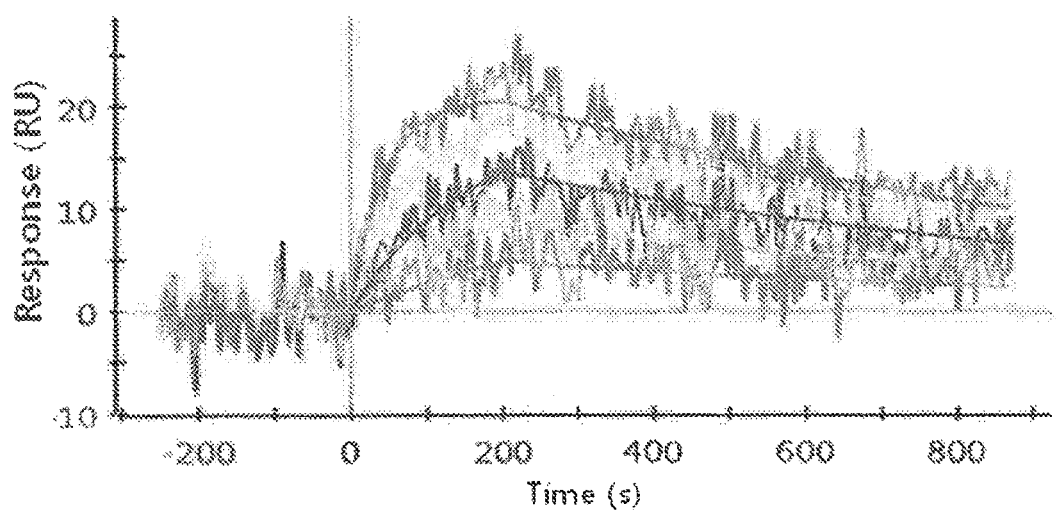

To achieve the above objects, the present disclosure provides an antibody, which can bind specifically to FcRn with high affinity in a pH-independent manner and is composed of a human-derived sequence, and thus causes little or no immune response when administered in vivo.

Antibodies according to the present disclosure are binding molecules having specificity for FcRn. The antibodies may include monoclonal antibodies (e.g., full-length antibodies having an immunoglobulin Fc domain), antibody compositions with polyepitopic specificity, bispecific antibodies, diabodies, and single-chain molecules, as well as antibody fragments (e.g., Fab, F(ab')2 and Fv), but are not limited thereto. The antibodies according to the present disclosure may be, for example, monoclonal antibodies against human FcRn.

The monoclonal antibodies include murine antibodies. Further, the monoclonal antibodies include "chimeric" antibodies in which a portion of the heavy and/or light chain is identical with or homologous to corresponding sequences in antibodies derived from a particular species such as mouse or belonging to a particular antibody class or subclass, while the remainder of the chain is identical with or homologous corresponding sequences in antibodies derived from another species or belonging to another antibody class or subclass such as human, as well as fragments of such antibodies, so long as they exhibit the desired biological activity. "Humanized antibodies" are used as a downstream set of "chimeric antibodies".

As an alternative to humanization, human antibodies can be generated. "Human antibodies" are antibodies that are produced by humans or have amino acid sequences corresponding to antibodies produced using any human antibody production technology. Human antibodies can be produced using various technologies known in the art, including phage display libraries. Human antibodies can be prepared by administering an antigen to a transgenic animal that has been modified to produce such antibodies in response to antigenic challenge, but whose endogenous loci have been disabled, e.g., immunized xenomice. Antibodies according to the present disclosure may be in the form of, for example, human antibodies.

Native four-chain antibodies are heterotetrameric glycoproteins composed of two identical light (L) chains and two identical heavy (H) chains. Each light chain has a variable domain at one end ($V_L$) and a constant domain at its other end. Each heavy chain has a variable domain ($V_H$) at the N-terminus, and has three constant domains (CH) for α and γ chains and four CH domains for μ and ε isotypes.

The term "variable" refers to the fact that certain portions of the variable domains differ extensively in sequence among antibodies. The V domain mediates antigen binding and defines the specificity of a particular antibody for its particular antigen. However, the variability is concentrated in three segments called hypervariable regions (HVRs) i.e. CDRs both in the light-chain and the heavy chain variable domains. The more highly conserved portions of variable domains are called the framework regions (FR). The light and heavy chain variable domains comprise from N- to C-terminus the domains FR1, CDR1, FR2, CDR2, FR3, CDR3 and FR4.

In the present disclosure, antibodies having affinity and specificity for human FcRn were obtained using human immunoglobulin transgenic animals. Transgenic animals can be produced by inactivating animal Ig germline genes and transplanting human Ig germline gene loci. The use of transgenic animals has an advantage in that an antibody is naturally optimized by the animal immune system without requiring affinity maturation so that an antibody drug having low immunogenicity and high affinity can be developed within a short time (US20090098134, US20100212035, Menoret et al, Eur J Immunol, 40:2932, 2010).

In the present disclosure, OmniRat™ (OMT, USA) having technology patented for human immunoglobulin transgenic rats was used. OmniRat™ can efficiently select an antibody having a high affinity for human FcRn, because it has a heavy chain composed of CH2 and CH3 domains that are from rat genes, and V, D and J regions and CH1 domain that are from human genes, and kappa light chain and lambda light chain from human, to efficiently select antibodies that have high affinity to human FcRn (Menoret et al, Eur J Immunol, 40:2932, 2010).

To obtain a monoclonal antibody having a high affinity for FcRn, a transgenic rat (OmniRat™) was immunized by injecting human FcRn therein, and then B cells were extracted from the cells and fused with myeloma cells to generate a hybridoma, after which the produced antibody was purified from the generated hybridoma.

The antibody according to the present disclosure acts as a non-competitive inhibitor of IgG in binding to FcRn. The binding of the antibody of the present disclosure to FcRn results in the inhibition of pathogenic antibody to FcRn, which promotes the clearance (i.e., removal) of pathogenic antibody from the body of the subject to reduce the half-life of the pathogenic antibody.

As used herein, the term "pathogenic antibody" means antibodies that cause pathological conditions or diseases. Examples of such antibodies include, but are not limited to, anti-platelet antibodies, anti-acetylcholine antibodies, anti-nucleic acid antibodies, anti-phospholipid antibodies, anti-collagen antibodies, anti-ganglioside antibodies, anti-desmoglein antibodies, etc.

The antibody or a fragment thereof according to the present disclosure has an advantage in that it makes it possible to non-competitively inhibit the binding of pathogenic antibody to FcRn at physiological pH (i.e., pH 7.0-7.4). FcRn binds to its ligand (i.e., IgG) and does not substantially show affinity for IgG at physiological pH rather than acidic pH. Thus, the anti-FcRn antibody that binds specifically to FcRn at physiological pH acts as a non-competitive inhibitor of the binding of IgG to FcRn, and in this case, the binding of the anti-FcRn antibody to FcRn is not influenced by the presence of IgG. Thus, the inventive antibody that binds to FcRn non-competitively with IgG in a pH-independent manner has an advantage over conventional competitive inhibitors (i.e., antibodies that bind to FcRn competitively with IgG) in that it can treat diseases even at significantly low concentrations by the FcRn-mediated signaling of IgG. In addition, in the procedure of intracellular migration in a state bound to FcRn, the anti-FcRn antibody according to the present disclosure maintains its binding to FcRn with an affinity higher than IgG in blood, and thus can inhibit the binding of IgG to FcRn even in endosomes that are acidic pH environments in which IgG can bind to FcRn, thereby promoting the clearance of IgG.

The antibody according to the present disclosure has an affinity for FcRn even in a physiological pH environment (i.e., pH 7.0-7.4) in which IgG does not bind to FcRn. At a pH of 6.0, the antibody of the present disclosure has a higher affinity for FcRn compared to serum IgG, suggesting that it acts as a non-competitive inhibitor.

In an embodiment of the present disclosure, the present disclosure is directed to an antibody binding specifically to FcRn or a fragment thereof comprising:

CDR1 comprising amino acid sequence, which has at least 90% homology with one or more amino acid sequence selected from the group consisting of SEQ ID No: 21, 24, 27, 30, 33, 36, 39 and 42;

CDR2 comprising amino acid sequence, which has at least 90% homology with one or more amino acid sequence selected from the group consisting of SEQ ID No: 22, 25, 28, 31, 34, 37, 40 and 43; and CDR3 comprising amino acid sequence, which has at least 90% homology with one or more amino acid sequence selected from the group consisting of SEQ ID No: 23, 26, 29, 32, 35, 38, 41 and 44.

Those skilled in the art will appreciate that the deletion, addition or substitution of some amino acids in the amino acid sequences set forth in the above SEQ ID Nos. also falls within the scope of the present disclosure.

In addition, sequences having a homology to the nucleotide sequences and amino acid sequences set described in the present disclosure within a certain range also fall within the scope of the present disclosure. "Homology" refers to similarity to at least one nucleotide sequence or amino acid sequence selected from the group consisting of SEQ ID Nos: 1 to 44, and include a homology of at least 90%. Preferably, homology might be at least 91%, at least 92%, at least 93%, at least 94%, at least 95%, at least 96%, at least 97%, at least 98% or at least 99%. The homology comparison is performed visually or using a known comparison program such as BLAST algorithm with standard settings. A commercially available program can express the homology between two or more sequences as a percentage. Homology (%) can be calculated for adjacent sequences.

Further, antibodies that bind specifically to FcRn having a KD (dissociation constant) of 0.01-2 nM: at pH 6.0 and pH 7.4 also fall within the scope of the present disclosure. "KD" as used herein refers to equilibrium dissociation constant for antibody-antigen binding, and may be calculated using the following equation: KD=kd/ka, wherein ka indicates association rate constant, and kd indicates dissociation rate constant. The measurement of kd or ka can be performed at 25° C. or 37° C.

In one example, the antibody of the present disclosure comprises: CDR1 comprising amino acid sequence of SEQ ID No: 21, CDR2 comprising amino acid sequence of SEQ ID No: 22 and CDR3 comprising amino acid sequence of SEQ ID No: 23, CDR1 comprising amino acid sequence of SEQ ID No: 27, CDR2 comprising amino acid sequence of SEQ ID No: 28 and CDR3 comprising amino acid sequence of SEQ ID No: 29, CDR1 comprising amino acid sequence of SEQ ID No: 33, CDR2 comprising amino acid sequence of SEQ ID No: 34 and CDR3 comprising amino acid sequence of SEQ ID No: 35, or CDR1 comprising amino acid sequence of SEQ ID No: 39, CDR2 comprising amino acid sequence of SEQ ID No: 40 and CDR3 comprising amino acid sequence of SEQ ID No: 41.

The amino acid sequences set forth in the above SEQ ID Nos. may be amino acid sequences corresponding to the CDR1 to CDR3 of the heavy-chain variable region.

In another example, the antibody or antigen-binding fragment of the present disclosure comprises:

CDR1 comprising amino acid sequence of SEQ ID No: 24, CDR2 comprising amino acid sequence of SEQ ID No: 25 and CDR3 comprising amino acid sequence of SEQ ID No: 26, CDR1 comprising amino acid sequence of SEQ ID No: 30, CDR2 comprising amino acid sequence of SEQ ID No: 31 and CDR3 comprising amino acid sequence of SEQ ID No: 32, CDR1 comprising amino acid sequence of SEQ ID No: 36, CDR2 comprising amino acid sequence of SEQ ID No: 37 and CDR3 comprising amino acid sequence of SEQ ID No: 38, or CDR1 comprising amino acid sequence of SEQ ID No: 42, CDR2 comprising amino acid sequence of SEQ ID No: 43 and CDR3 comprising amino acid sequence of SEQ ID No: 44.

The amino acid sequences set forth in the above SEQ ID Nos. may be amino acid sequences corresponding to the CDR1 to CDR3 of the light-chain variable region.

Specifically, the antibody or antigen-binding fragment of the present disclosure comprises: one or more heavy chain variable region and light chain variable region selected from the group consisting of:

heavy chain variable region comprising CDR1 comprising amino acid sequence of SEQ ID No: 21, CDR2 comprising amino acid sequence of SEQ ID No: 22 and CDR3 comprising amino acid sequence of SEQ ID No: 23, and light chain variable region comprising CDR1 comprising amino acid sequence of SEQ ID No: 24, CDR2 comprising amino acid sequence of SEQ ID No: 25 and CDR3 comprising amino acid sequence of SEQ ID No: 26;

heavy chain variable region comprising CDR1 comprising amino acid sequence of SEQ ID No: 27, CDR2 comprising amino acid sequence of SEQ ID No: 28 and CDR3 comprising amino acid sequence of SEQ ID No: 29, and light chain variable region comprising CDR1 comprising amino acid sequence of SEQ ID No: 30, CDR2 comprising amino acid sequence of SEQ ID No: 31 and CDR3 comprising amino acid sequence of SEQ ID No: 32;

heavy chain variable region comprising CDR1 comprising amino acid sequence of SEQ ID No: 33, CDR2 comprising amino acid sequence of SEQ ID No: 34 and CDR3 comprising amino acid sequence of SEQ ID No: 35, and light chain variable region comprising CDR1 comprising amino acid sequence of SEQ ID No: 36, CDR2 comprising amino acid sequence of SEQ ID No: 37 and CDR3 comprising amino acid sequence of SEQ ID No: 38; and heavy chain variable region comprising CDR1 comprising amino acid sequence of SEQ ID No: 39, CDR2 comprising amino acid sequence of SEQ ID No: 40 and CDR3 comprising amino acid sequence of SEQ ID No: 41, and light chain variable region comprising CDR1 comprising amino acid sequence of SEQ ID No: 42, CDR2 comprising amino acid sequence of SEQ ID No: 43 and CDR3 comprising amino acid sequence of SEQ ID No: 44.

In one example, the antibody or antigen-binding fragment of the present disclosure comprises one or more heavy chain variable region and light chain variable region comprising one or more amino acid sequence selected from the group consisting of amino acid sequences of SEQ ID No: 2, 4, 6, 8, 10, 12, 14, 16, 18 and 20.

Specifically, the antibody or antigen-binding fragment of the present disclosure comprises heavy chain variable region comprising amino acid sequence of SEQ ID No: 2, 4, 6, 8, or 10, and/or light chain variable region comprising amino acid sequence of SEQ ID No: 12, 14, 16, 18 or 20.

In detail, the antibody or antigen-binding fragment of the present disclosure comprises one or more heavy chain variable region and light chain variable region selected from the group consisting of:

heavy chain variable region comprising amino acid sequence of SEQ ID No: 2 and light chain variable region comprising amino acid sequence of SEQ ID No: 12;

heavy chain variable region comprising amino acid sequence of SEQ ID No: 4 and light chain variable region comprising amino acid sequence of SEQ ID No: 14;

heavy chain variable region comprising amino acid sequence of SEQ ID No: 6 and light chain variable region comprising amino acid sequence of SEQ ID No: 16;

heavy chain variable region comprising amino acid sequence of SEQ ID No: 8 and light chain variable region comprising amino acid sequence of SEQ ID No: 18; and heavy chain variable region comprising amino acid sequence of SEQ ID No: 10 and light chain variable region comprising amino acid sequence of SEQ ID No: 20.

"Fragment" or "antibody fragment" as the terms are used herein in reference to an antibody refer to a polypeptide derived from an antibody polypeptide molecule (e.g., an antibody heavy or light chain polypeptide) that does not comprise a full length antibody polypeptide, but which still comprises at least a portion of a full length antibody polypeptide. Antibody fragments often comprise polypeptides that comprise a cleaved portion of a full length antibody polypeptide, although the term is not limited to such cleaved fragments. Since a fragment, as the term is used herein in reference to an antibody, encompasses fragments that comprise single polypeptide chains derived from antibody polypeptides (e.g. a heavy or light chain antibody polypeptides), it will be understood that an antibody fragment may not, on its own, bind an antigen.

Fragments of the antibody according to the present disclosure include, but are not limited to, single-chain antibodies, bispecific, trispecific, and multispecific antibodies such as diabodies, triabodies and tetrabodies, Fab fragments, F(ab')$_2$ fragments, Fd, scFv, domain antibodies, dual-specific antibodies, minibodies, scap (sterol regulatory binding protein cleavage activating protein), chelating recombinant antibodies, tribodies or bibodies, intrabodies, nanobodies, small modular immunopharmaceuticals (SMIP), binding-domain immunoglobulin fusion proteins, camelized antibodies, VHH containing antibodies, IgD antibodies, IgE antibodies, IgM antibodies, IgG1 antibodies, IgG2 antibodies, IgG3 antibodies, IgG4 antibodies, derivatives in antibody constant regions, and synthetic antibodies based on protein scaffolds, which have the ability to bind to FcRn. It will be obvious to those skilled in the art that any fragment of the antibody according to the present disclosure will show the same properties as those of the antibody of the present disclosure.

In addition, antibodies having a mutation in the variable region are included in the scope of the present disclosure. Examples of such antibodies include antibodies having a conservative substitution of an amino acid residue in the variable region. As used herein, the term "conservative substitution" refers to substitution with another amino acid residue having properties similar to those of the original amino acid residue. For example, lysine, arginine and histidine have similar properties in that they have a basic side-chain, and aspartic acid and glutamic acid have similar properties in that they have an acidic side chain. In addition, glycine, asparagine, glutamine, serine, threonine, tyrosine, cysteine and tryptophan have similar properties in that they have an uncharged polar side-chain, and alanine, valine, leucine, threonine, isoleucine, proline, phenylalanine and methionine have similar properties in that they have a non-polar side-chain. Also, tyrosine, phenylalanine, tryptophan and histidine have similar properties in that they have an aromatic side-chain. Thus, it will be obvious to those skilled in the art that, even when substitution of amino acid residues in groups showing similar properties as described above occurs; it will show no particular change in the properties. Accordingly, antibodies having a mutation caused by conservative substitution in the variable region are included in the scope of the present disclosure.

In addition, the antibody according to the present disclosure or its fragment may be used as a conjugate with another substance. Substances that may be used as conjugates with the antibody according to the present disclosure or its fragment include therapeutic agents that are generally used for the treatment of autoimmune diseases, substances capable of inhibiting the activity of FcRn, and a moiety that is physically associated with the antibody to improve its stabilization and/or retention in circulation, for example, in blood, serum, lymph, or other tissues. For example, the FcRn-binding antibody can be associated with a polymer, e.g., a non-antigenic polymer such as polyalkylene oxide or polyethylene oxide. Suitable polymers will vary substantially by weight. Polymers having molecular number average weights ranging from about 200 to about 35,000 (or about 1,000 to about 15,000, and 2,000 to about 12,500) can be used. For example, the FcRn-binding antibody can be conjugated to water soluble polymers, e.g., hydrophilic polyvinyl polymers, e.g. polyvinylalcohol polyvinylpyrrolidone. A non-limiting list of such polymers includes, but is not limited to, polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In another embodiment, the present disclosure is directed to a pharmaceutical composition for treating autoimmune disease comprising the anti-FcRn antibody, and one or more pharmaceutically acceptable carriers. Also, the present disclosure is directed to a method of treating autoimmune disease comprising administering an effective amount of antibody binding specifically to FcRn to a patient in need thereof.

The pharmaceutical composition may comprise a pharmaceutically acceptable carrier, excipient, and the like, which are well known in the art. The pharmaceutically acceptable carriers should be compatible with the active ingredient such as the antibody or a fragment thereof according to the present disclosure and may be physiological saline, sterile water, Ringer's solution, buffered saline, dextrose solution, maltodextrin solution, glycerol, ethanol, or a mixture of two or more thereof. In addition, the pharmaceutical composition of the present disclosure may, if necessary, comprise other conventional additives, including antioxidants, buffers, and bacteriostatic agents. Further, the pharmaceutical composition of the present disclosure may be formulated as injectable forms such as aqueous solutions, suspensions or emulsions with the aid of diluents, dispersants, surfactants, binders and lubricants. In addition, the pharmaceutical composition of the present disclosure may be provided by formulating into a various form such as powder, tablet, capsule, liquid, inject, ointment, syrup, etc., and single-dosage or multi-dosage container such as sealed ample or vial.

The pharmaceutical composition of the present disclosure may be applied to all autoimmune diseases that are mediated by IgG and FcRn, and typical examples of such autoimmune diseases include, but are not limited to, immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa acquisita, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, lupus, idiopathic thrombocytopenic purpura, lupus nephritis and membranous nephropathy.

In the treatment method according to the present disclosure, the dose of the antibody can be suitably determined by taking into consideration the patient's severity, condition, age, case history and the like. For example, the antibody may be administered at a dose of 1 mg/kg to 2 g/kg. The antibody may be administered once or several times.

The present disclosure also provides a method for ameliorating an autoimmune or autoimmune condition, including administering the antibody of the present disclosure or a fragment of the antibody to a subject in need of treatment. The present disclosure also provides a specific anti-FcRn therapy.

The inventive method for ameliorating an autoimmune or autoimmune condition or the inventive anti-FcRn therapy can be achieved by administering the pharmaceutical composition of the present disclosure to a subject. The pharmaceutical composition of the present disclosure can be administered orally or parenterally. The pharmaceutical composition according to the present disclosure can be administered by various routes, including, but not limited to, oral, intravenous, intramuscular, intra-arterial, intramedullary, intradural, intracardial, transdermal, subcutaneous, intraperitoneal, gastrointestinal, sublingual, and local routes. The dose of the composition of the present disclosure may vary depending on various factors, such as a patient's body weight, age, sex, health condition and diet, the time and method of administration, excretion rate, and severity of a disease, and may be easily determined by a person of ordinary skill in the art. Generally, 1-200 mg/kg, and preferably, 1-40 mg/kg of the composition may be administered to patients afflicted with autoimmune or autoimmune conditions, and these regimens are preferably designed to reduce the serum endogenous IgG concentration to less than 75% of pretreatment values. Intermittent and/or chronic (continuous) dosing strategies may be applied in view of the conditions of patients.

In another embodiment, the present disclosure also provides a diagnostic composition comprising the antibody of the present disclosure or a fragment thereof, and a diagnostic method that uses the diagnostic composition. In other words, the antibody of the present disclosure or a fragment thereof, which binds to FcRn, has in vitro and in vivo diagnostic utilities.

In another embodiment, the present disclosure is directed to a composition for detecting FcRn comprising the anti-FcRn antibody or a fragment thereof. The present disclosure also provides a method, system or device for detecting FcRn in vivo or in vitro comprising treating the anti-FcRn antibody.

The in vitro detection method, system or device might, for example, include (1) bringing a sample into contact with the FcRn-binding antibody; (2) detecting the formation of a complex between the FcRn-binding antibody and the sample; and/or (3) bringing a reference sample (e.g., a control sample) into contact with the antibody; and (4) determining the degree of formation of the complex between the antibody and the sample by comparison with that in the reference sample. A change (e.g., a statistically significant change) in the formation of the complex in the sample or the subject as compared to that in the control sample or subject indicates the presence of FcRn in the sample.

The in vivo detection method, system or device may include: (1) administering the FcRn-binding antibody to a subject; and (2) detecting the formation of a complex between the FcRn-binding antibody and the subject. The detecting may include determining location or time of formation of the complex. The FcRn-binding antibody can be directly or indirectly labeled with a detectable substance to facilitate detection of the bound or unbound antibody. Suitable detectable substances include various enzymes, prosthetic groups, fluorescent materials, luminescent materials, and radioactive materials. The formation of a complex between the FcRn-binding antibody and FcRn can be detected by measuring or visualizing the antibody bound or not bound to FcRn. A conventional detection assay, for example, enzyme-linked immunosorbent assay (ELISA), radioimmunoassay (RIA) or tissue immunohistochemistry may be used. In addition to labeling of the FcRn-binding antibody, the presence of FcRn can be assayed in a sample by competition immunoassay using a standard labeled with a detectable substance and an unlabeled FcRn-binding antibody. In one example of this assay, the biological sample, the labeled standard and the FcRn-binding antibody are combined and the amount of labeled standard unbound to FcRn is determined. The amount of FcRn in the biological sample is inversely proportional to the amount of labeled standard unbound to FcRn.

For detection purposes, the antibody of the present disclosure or a fragment thereof can be labeled with a fluorophore and a chromophore. Because antibodies and other proteins absorb light having wavelengths up to about 310 nm, the fluorescent moieties should be selected to have substantial absorption at wavelengths above 310 nm and preferably above 400 nm. The antibody of the present disclosure or a fragment thereof can be labeled with a variety of suitable fluorescers and chromophores. One group of fluorescers xanthene dyes, which include fluoresceins and rhodamines. Another group of fluorescent compounds are naphthylamines. Once labeled with a fluorophore or chromophore, the antibody can be used to detect the presence or localization of the FcRn in a sample, e.g., using fluorescent microscopy (such as confocal or deconvolution microscopy).

Detection of the presence or localization of FcRn using the antibody of the present disclosure or a fragment thereof can be performed by various methods such as histological analysis, protein arrays and FACS (Fluorescence Activated Cell Sorting).

In the present disclosure, the presence of FcRn or FcRn-expressing tissue in vivo can be performed by an in vivo Imaging method. The method includes (i) administering to a subject (e.g., a patient having an autoimmune disorder) an anti-FcRn antibody, conjugated to a detectable marker; and (ii) exposing the subject to a means for detecting said detectable marker to toe FcRn-expressing tissues or cells. For example, the subject is imaged, e.g., by NMR or other tomographic means. Examples of labels useful for diagnostic imaging include radiolabels, fluorescent labels, positron emitting isotopes, chemiluminescers, and enzymatic markers. A radiolabeled antibody can also be used for in vitro diagnostic tests. The specific activity of an isotopically-labeled antibody depends upon the half-life, the isotopic purity of the radioactive label, and how the label is incorporated into the antibody.

The present disclosure also provides a kit comprising an antibody that binds to FcRn a fragment thereof and instructions for diagnostic use, e.g., the use of the FcRn-binding antibody or a fragment thereof, to detect FcRn, in vitro, e.g., in a sample, e.g., a biopsy or cells from a patient having an autoimmune disorder, or in vivo, e.g., by imaging a subject. The kit can further contain at least one additional reagent, such as a label or additional diagnostic agent. For in vivo use, the antibody can be formulated as a pharmaceutical composition.

In another embodiment, the present disclosure is directed to polynucleotide sequences that encode the antibody of the present disclosure or a fragment thereof.

In an example, a polynucleotide sequence that encodes the antibody of the present disclosure or a fragment thereof is a sequence, which has at least 90% homology with one or more sequence selected from the group consisting of SEQ ID No: 1, 3, 5, 7, 9, 11, 13, 15, 17 and 19 or sequence having a homology of more than 90%, when compared with the sequences mentioned above.

Specifically, a polynucleotide sequence of the antibody of the present disclosure or a fragment thereof is a sequence that encodes heavy chain of the antibody of the present disclosure is SEQ ID No: 1, 3, 5, 7 or 9, and/or a sequence that encodes light chain of the antibody of the present disclosure is SEQ ID No: 11, 13, 15, 17 or 19.

In another embodiment, the present disclosure is directed to a recombinant expression vector comprising the polynucleotide, host cell, which is transfected with the recombinant expression vector and method of preparing an antibody binding specifically to FcRn or a fragment thereof by using the recombinant expression vector and host cell.

In one embodiment, the antibody or a fragment thereof according to the present disclosure is preferably produced by expression and purification using a gene recombination method. Specifically, the variable regions that encode the inventive antibody that binds specifically to FcRn are produced by being expressed in separate host cells or simultaneously in a single host cell.

As used herein, the term "recombinant vector" refers to an expression vector capable of expressing the protein of interest in a suitable host cell and means a DNA construct including essential regulatory elements operably linked to express a nucleic acid insert. As used herein, the term "operably linked" means that a nucleic acid expression control sequence is functionally linked to a nucleic acid sequence encoding the protein of interest so as to execute general functions. Operable linkage with the recombinant vector can be performed using a gene recombination technique well known in the art, and site-specific DNA cleavage and ligation can be easily performed using enzymes generally known in the art.

A suitable expression vector that may be used in the present disclosure may include expression regulatory elements such as a promoter, an operator, an initiation codon, a stop codon, a polyadenylation signal, and an enhancer, as well as a signal sequence for membrane targeting or secretion. The initiation and stop codons are generally considered as part of a nucleotide sequence encoding the immunogenic target protein, and are necessary to be functional in an individual to whom a genetic construct has been administered, and must be in frame with the coding sequence. Promoters may generally be constitutive or inducible. Prokaryotic promoters include, but are not limited to, lac, tac, T3 and T7 promoters. Eukaryotic promoters include, but are not limited to, simian virus 40 (SV40) promoter, mouse mammary tumor virus (MMTV) promoter, human immunodeficiency virus (HIV) promoter such as the HIV Long Terminal Repeat (LTR) promoter, moloney virus promoter, cytomegalovirus (CMV) promoter, epstein barr virus (EBV) promoter, rous sarcoma virus (RSV) promoter, as well as promoters from human genes such as human β-actin, human hemoglobin, human muscle creatine and human metallothionein. The expression vector may include a selectable marker that allows selection of host cells containing the vector. Genes coding for products that confer selectable phenotypes, such as resistance to drugs, nutrient requirement, resistance to cytotoxic agents or expression of surface proteins, are used as general selectable markers. Since only cells expressing a selectable marker survive in the environment treated with a selective agent, transformed cells can be selected. Also, a replicable expression vector may include a replication origin, a specific nucleic acid sequence that initiates replication. Recombinant expression vectors that may be used in the present disclosure include various vectors such as plasmids, viruses and cosmids. The kind of recombinant vector is not specifically limited and the recombinant vector could function to express a desired gene and produce a desired protein in various host cells such as prokaryotic and eukaryotic cells. However, it is preferred to use a vector that can produce a large amount of a foreign protein similar to a natural protein while having strong expression ability with a promoter showing strong activity.

In the present disclosure, a variety of expression host/vector combinations may be used to express the antibody or a fragment thereof according to the present disclosure. For example, expression vectors suitable for the eukaryotic host include, but are not limited to, SV40, bovine papillomavirus, adenovirus, adeno-associated virus, cytomegalovirus, and retrovirus. Expression vectors that may be used for bacterial hosts include bacterial plasmids such as pET, pRSET, pBluescript, pGEX2T, pUC, col E1, pCR1, pBR322, pMB9 and derivatives thereof, a plasmid such as RP4 having a wider host range, phage DNA represented as various phage lambda derivatives such as gt10, gt11 and NM989, and other DNA phages such as M13 and filamentous single-stranded DNA phage. Expression vectors useful in yeast cells include 2 μm plasmid and derivatives thereof. A vector useful in insect cells is pVL941.

The recombinant vector is introduced into a host cell to form a transformant. Host cells suitable for use in the present disclosure include prokaryotic cells such as E. coli, Bacillus subtilis, Streptomyces sp., Pseudomonas sp., Proteus mirabilis and Staphylococcus sp., fungi such as Aspergillus sp., yeasts such as Pichia pastoris, Saccharomyces cerevisiae, Schizosaccharomyces sp., and Neurospora crassa, and eukaryotic cells such as lower eukaryotic cells, and higher other eukaryotic cells such as insect cells.

Host cells that may be used in the present disclosure are preferably derived from plants and mammals, and examples thereof include, but are not limited to, monkey kidney cells (COS 7), NSO cells, SP2/0, Chinese hamster ovary (CHO) cells, W138, baby hamster kidney (BHK) cells, MDCK, myeloma cells, HuT 78 cells and HEK293 cells. Preferably, CHO cells are used.

In the present disclosure, transfection or transformation into a host cell includes any method by which nucleic acids can be introduced into organisms, cells, tissues or organs, and, as known in the art, may be performed using a suitable standard technique selected according to the kind of host cell. These methods include, but are not limited to, electroporation, protoplast fusion, calcium phosphate ($CaPO_4$) precipitation, calcium chloride ($CaCl_2$) precipitation, agitation with silicon carbide fiber, and agrobacterium-, PEG-, dextran sulfate-, lipofectamine- and desiccation/inhibition-mediated transformation.

The FcRn-specific antibody or a fragment thereof according to the present disclosure can be produced in large amounts by culturing the transformant comprising the recombinant vector in nutrient medium, and the medium and culture conditions that are used in the present disclosure can be suitable selected depending on the kind of host cell. During culture, conditions, including temperature, the pH of medium, and culture time, can be controlled so as to be suitable for the growth of cells and the mass production of protein. The antibody or antibody fragment produced by the recombination method as described can be collected from the medium or cell lysate and can be isolated and purified by conventional biochemical isolation techniques (Sambrook et al., Molecular Cloning: A laboratory Manual, 2nd Ed., Cold Spring Harbor Laboratory Press (1989); Deuscher, M., Guide to Protein Purification Methods Enzymology, Vol. 182. Academic Press. Inc., San Diego, Calif. (1990)). These techniques include, but are not limited to, electrophoresis, centrifugation, gel filtration, precipitation, dialysis, chromatography (ion exchange chromatography, affinity chromatography, immunosorbent chromatography, size exclusion chromatography, etc.), isoelectric point focusing, and various modifications and combinations thereof. Preferably, the antibody or the antibody fragment is isolated and purified using protein A.

The antibodies of the present disclosure showed antigen binding abilities (KD values) from about 300 μM or less to about 2 nM or less at pH 7.4, and also showed KD values from 2 nM or less to 900 μM or less at pH 6.0. The antibodies of the present disclosure have a strong hFcRn binding affinity of 0.01-2 nM and thus it is believed that the antibodies bound to the outside of cells maintain even their binding to endosomes, suggesting that these antibodies have an excellent effect of blocking the binding of autoantibodies to hFcRn. In addition, this effect of blocking the binding of autoantibodies to hFcRn was also confirmed in a blocking assay performed using human FcRn-expressing cells and FACS.

EXAMPLES

Hereinafter, the present disclosure will be described in further detail with reference to examples. It will be obvious to a person having ordinary skill in the art that these

Example 1

Construction of Anti-FcRn-Expressing Library Using Transgenic Rats

Immunization was performed using a total of six transgenic rats (OmniRat®, OMT). As an immunogen, human FcRn was used. Both footpads of the rats were immunized eight times with 0.0075 mg of human FcRn (each time) together with an adjuvant at 3-day intervals for 24 days. On day 28, the rats were immunized with 5-10 μg of the immunogen diluted in PBS buffer. On day 28, rat serum was collected and used to measure the antibody titer. On day 31, the rats were euthanized, and the popliteal lymph node and the inguinal lymph node were recovered for fusion with P3X63/AG8.653 myeloma cells.

ELISA analysis was performed to measure the antibody titer in rat serum. Specifically, human FcRn was diluted in PBS (pH 6.0 or pH 7.4) buffer to make 2 μg/mL of a solution, and 100 μl of the solution was coated on each well of a 96-well plate, and then incubated at 4° C. for at least 18 hours. Each well was washed three times with 300 μL of washing buffer (0.05% Tween 20 in PBS) to remove unbound human FcRn, and then 200 μL of blocking buffer was added to each well and incubated at room temperature for 2 hours. A test serum sample was diluted at 1/100, and then the solution was serially 2-fold diluted to make a total of 10 test samples having a dilution factor of 1/100 to 1/256,000). After blocking, each well was washed with 300 μL of washing buffer, and then each test sample was added to each cell and incubated at room temperature for 2 hours. After washing three times, 100 μL of a 1:50,000 dilution of secondary detection antibody in PBS buffer was added to each well and incubated at room temperature for 2 hours. After washing three times again, 100 μL of TMB solution was added to each well and allowed to react at room temperature for 10 minutes, and then 50 μL of 1M sulfuric acid-containing stop solution was added to each well to stop the reaction, after which the OD value at 450 nm was measured with a microplate reader. Regarding the anti-hFcRn IgG titer resulting from immunization was higher than that in the pre-immune serum of the rats, which was not immunized with the OD value at 450 nm in the 1/100 dilution condition 1.0 or higher, suggesting that the rats were well immunized.

A total of three hybridoma libraries A, B and C fused using polyethylene glycol were made. Specifically, transgenic rats 1 and 5 were used to make hybridoma library A, and rats 2 and 6 were used to make hybridoma library B, and rats 3 and 4 were used to make hybridoma library C. A hybridoma library fusion mixture for constructing each hybridoma library was cultured in HAT-containing medium for 7 days so that only cells fused to HAT would be selected. Hybridoma cells viable in the HAT medium were collected and cultured in HT media for about 6 days, and then the supernatant was collected, and the amount of rat IgG in the supernatant was measured using a rat IgG ELISA kit (RD-biotech). Specifically, each sample was diluted at 1:100, and 100 μL of the dilution was added to each well of an ELISA plate and mixed with peroxidase-conjugated anti-rat IgG, followed by reaction at room temperature for 15 minutes. 100 μL of TMB solution was added to each well and allowed to react at room temperature for 10 minutes, and then 50 μL of 1M sulfuric acid-containing stop solution was added to each well to stop the reaction. Next, the OD value at 450 nm was measured with a microplate reader.

Example 2

Evaluation of the Antigen Binding Affinity and IgG Binding Blocking Ability of Anti-hFcRn Antibodies of Hybridoma Libraries To analyze the binding of antibodies to human FcRn, the same ELISA analysis (pH 6.0 and pH 7.4) as mentioned above was performed. The results of evaluation of the hFcRn binding of the three hybridoma libraries A, B and C indicates that the hFcRn binding affinity was higher in the order of A>C>B at both pH 6.0 and pH 7.4.

Using the culture supernatants of the three hybridoma libraries, the evaluation of the hFcRn binding affinity by FACS at 5 ng/mL and 25 ng/mL was performed at pH 6.0 and pH 7.4. Human FcRn-stable expressing HEK293 cells were detached from a flask, and then suspended in reaction buffer (0.05% BSA in PBS, pH 6.0 or pH 7.4). The suspension was diluted to a cell density of $2 \times 10^6$ cells/mL, and 50 μL of the dilution was added to each well of a 96-well plate. Then, 50 μL of the hybridoma library culture supernatant diluted to each of 10 ng/mL and 50 ng/mL was added to each well and suspended to allow antibody to bind. A488 rabbit anti-IgG goat antibody was diluted at 1:200 in reaction buffer, and 100 μL of the dilution was added to each well and mixed with the cell pellets to perform a binding reaction, and then 150 μL of reaction buffer was added to each well. Measurement was performed in FACS (BD). Like the ELISA results, it could be seen that hybridoma library A showed the highest binding affinity.

Evaluation of the human FcRn blocking ability of the hybridoma library by FACS was performed at pH 6.0. Specifically, naïve HEK293 cells and human FcRn-overexpressing HEK293 cells were suspended in reaction buffer (0.05% BSA in PBS, pH 6.0). $1 \times 10^5$ cells were added to a 96-well plate, and treated with each of 4 nM of each hybridoma library culture supernatant and 0.4 nM of a 10-fold dilution of the supernatant. To confirm the hIgG blocking ability, 100 nM A488-hIgG1 was added to each well, and then incubated on ice for 90 minutes. After completion of the reaction, the cell pellets were washed with 100 μL of reaction buffer, and transferred into a U-shaped round bottom tube, followed by measurement in FACS. The amount of 100 nM A488-hIgG1 remaining in the human FcRn-overexpressing stable cells was measured, and then the blocking was calculated. As an isotype control, hIgG1 was used, and as a positive control, previously developed HL161-1Ag antibody was used to comparatively evaluate the antibody blocking effect. Each control was analyzed at concentrations of 1 μM and 2 μM, and the hybridoma library sample was measured at two concentrations of 0.4 nM and 4 nM. As a result, it was found that hybridoma library A showed the highest blocking effect.

Example 3

Isolation of Hybridoma Clone by FACS and Selection of Human Antibodies

Using hybridoma library A showing the highest human FcRn binding affinity and blocking effect, clones were isolated by FACS (flow cytometry) to thereby obtain a total of 442 single clones. The isolated monoclones were cultured in HT media, and the supernatant was collected. Antibody-expressing hybridoma clones binding to hFcRn in the supernatant were selected by FACS. As a result, it could be seen that 100 clones (M1-M100) did strongly bind to the hFcRn-expressing HEK293 cells.

RNA was isolated from the 100 monoclones selected by FACS analysis and the isolated RNA was sequenced. In the first-step sequencing, 88 of the 100 monoclones were sequenced, and divided according to the amino acid sequence into a total of 35 groups (G1 to G38). The culture supernatants of the representative clones of 33 groups excluding two clones (G33 and G3) whose media were not available were diluted at a concentration of 100 ng/mL, and the binding affinity for hFcRn was evaluated by ELISA.

In the same manner as described above, evaluation of the hFcRn binding affinity by SACS was performed at pH 6.0 and 7.4. The order of the binding affinity of the clones was similar between the pHs, and the binding intensity appeared at various levels.

In addition, evaluation of the hFcRn blocking effects of the 33 clones was performed by FACS at pH 6.0. The blocking was calculated based on the measured MFI value. Based on the results of analysis of the blocking % at a concentration of 1667 pM, the clones were divided into a total of the following four groups: group A: 70-100%; group B: 30-70%; group C: 10-30%; and group D: 10% or less.

For kinetic analysis of the hybridoma clones by SPR, human FcRn was immobilized, and then the analysis was performed using the hybridoma culture as an analyte. Most of the clones excluding several clones showed a $k_{on}$ of $10^6$ M or higher and a $k_{off}$ value of $10^{-3}$ M or lower. In conclusion, it was shown that all the clones had a KD value of $10^{-9}$ to $10^{-11}$ M.

Among the five hybridoma clones, the genes of 18 clones having no N-glycosylation site or free cysteine in the CDR sequences of groups A and B divided according to the results of analysis of the hFcRn blocking effect were converted to whole human IgG sequences.

Specifically, the amino acid sequence similarity between the VH and VL of the 18 selected antibodies and the human germ line antibody group was examined using the Ig BLAST program of the NCBI webpage.

In order to clone the 18 human antibody genes, restriction enzyme recognition sites were inserted into both ends of the genes in the following manner. EcoRI/ApaI were inserted into the heavy-chain variable domain (VH); EcoRI/XhoI were inserted into the light-chain lambda variable domain (VL(λ)); EcoRI/NheI restriction enzyme recognitions sites were inserted into the light-chain kappa variable domain (VL(κ)). In the case of the light-chain variable domain, the light-chain lambda variable (VL(λ)) gene sequence was linked to the human light-chain constant (LC(λ)) region gene during gene cloning, and the light-chain kappa variable (VL(κ)) gene sequence was linked to the human light-chain constant (LC(κ)) region gene.

In cloning into pCHO1.0 expression vectors for expression of antibodies in animal cells, the light-chain and heavy-chain genes were inserted after cleavage with EcoRV, PacI, AvrII and BstZ17I restriction enzymes. In order to examine whether pCHO1.0 expression vectors containing the 18 selected human antibody genes were consistent with the synthesized gene sequences, DNA sequencing was performed.

Using the pCHO1.0 expression vectors that are animal cell expression systems containing all the antibody light-chain and heavy-chain genes, whole human IgG was expressed. The human antibody was obtained by transiently transfecting the plasmid DNA of each of the antibodies into CHO-S cells and purifying the antibody, secreted into the medium, by protein A column.

Human IgG was injected into hFcRn-expressing Tg32 (hFcRn+/+, hβ2m+/+, mFcRn−/−, mβ2m−/−) mice (Jackson Laboratory), and then the human antibodies converted to the human IgG sequences were administered to the mice in order to examine whether the antibodies would influence the catabolism of human IgG.

Based on the in vitro analysis results for binding affinity (KD) for the antigen and the analysis of human FcRn binding affinity and blocking effect by FACS, and the in vivo analysis of catabolism of human IgG, four human anti-FcRn antibody proteins (HL161A, HL161B, HL161C and HL161D) that most effectively acted were selected (FIG. 1). In addition, an HL161BK antibody having no N-glycosylation site was prepared by substituting asparagine (N) at position 83 of the heavy-chain variable framework of the HL161B antibody with lysine (K). The nucleotide sequences, amino acid sequences and CDR sequences of the light-chain and heavy-chain variable regions of each antibody are shown in Tables 1, 2 and 3.

TABLE 1

Polynucleotide sequences of heavy-chain and light-chain variable domains of selected human FcRn antibodies

| Antibody name | Heavy-chain variable domain sequence | | Light-chain variable domain sequence | |
|---|---|---|---|---|
| | SEQ ID NO. | Polynucleotide sequence | SEQ ID NO. | Polynucleotide sequence |
| HL161A | 1 | GAAGTGCAGC TGCTGGAATC CGGCGGAGGC CTGGTGCAGC CTGGCGGCTC TCTGAGACTG TCCTGCGCCG CCTCCAGTT CACCTTCGGC AGCTGCGTGA TGACCTGGGT CCGACAGGCT CCCGGCAAGG GCCTGGAATG GGTGTCCGTG ATCTCCGGCT CCGGCGGCTC CACCTACTAC GCCGACTCTG TGAAGGGCCG GTTCACCATC TCCCGGGACA ACTCCAAGAA CACCCTGTAC CTGCAGATGA ACTCCCTGCG GGCCaAGGAC ACCGCCGTGT | 11 | TCTTACGTGC TGACCCAGCC CCCCTCCGTG TCTGTGGCTC CTGGCCAGAC CGCCAGAATC ACCTGTGGCG GCAACAACAT CGGCTCCACC TCCGTGCACT GGTATCAGCA GAAGCCCGGC CAGGCCCCCG TGCTGGTGGT GCACGACGAC TCCGACCGGC CTTCTGGCAT CCCTGAGCGG TTCTCCGGCT CCAACTCCGG CAACACCGCC ACCCTGACCA TCTCCAGAGT GGAAGCCGGC GACGAGGCCG ACTACTACTG CCAAGTGCGA GACTCCTCCT |

TABLE 1-continued

Polynucleotide sequences of heavy-chain and light-chain variable domains of selected human FcRn antibodies

| Antibody name | Heavy-chain variable domain sequence SEQ ID NO. | Polynucleotide sequence | Light-chain variable domain sequence SEQ ID NO. | Polynucleotide sequence |
|---|---|---|---|---|
| | | ACTACTGCGC CAAGACCCCC TGGTGGCTGC GGTCCCCCTT CTTCGATTAC TGGGGCCAGG GCACCCTGGT GACAGTGTCC TCC | | CCGACCACGT GATCTTCGGC GGAGGCACCA AGCTGACCGT GCTGGGCCAG CCTAAGGCCG CTCCCTCCGT GACCCTG |
| HL161B | 3 | CAACTGTTGC TCCAGGAATC CGGTCCTGGT CTTGTAAAGC CATCTGAGAC TCTCTCCCTT ACCTGTACCG TTAGCGGAGG AAGTCTTTCG TCAAGCTTCT CCTACTGGGT GTGGATCAGA CAGCCTCCCG GAAAAGGGTT GGAGTGGATT GGCACAATAT ACTACTCCGG CAACACTTAC TATAACCCCA GCCTGAAGAG CAGGCTGACT ATCTCTGTCG ACACCAGTAA AAATCACTTT TCTCTGAATC TGTCTTCAGT GACCGCAGCC GACACCGCCG TGTATTATTG CGCTCGGCGC GCCGGGATTC TGACAGGCTA TCTGGATTCA TGGGGCCAGG GGACATTGGT TACAGTGTCT AGT | 13 | TCTTACGTGC TGACCCAGTC CCCCTCCGTG TCCGTGGCTC CTGGCCAGAC CGCCAGAATC ACCTGTGGCG GCAACAACAT CGGCTCCAAG TCCGTGCACT GGTATCAGCA GAAGCCCGGC CAGGCCCCCG TGCTGGTGGT GTACGACGAC TCCGACCGGC CCTCTGGCAT CCCTGAGCGG TTCTCCGCCT CCAACTCCGG CAACACCGCC ACCCTGACCA TCTCCAGAGT GGAAGCCGGC GACGAGGCCG ACTACTACTG CCAAGTGTGG GACTCCTCCT CCGACCACGT GGTGTTCGGC GGAGGCACCA AGCTGACCGT GCTGGGCCAG CCTAAGGCCG CTCCCTCCGT GACCCTG |
| HL161BK | 5 | CAGCTGCTGC TGCAAGAATC CGGCCCTGCC CTGGTGAAAC CCTCCGAGAC ACTGTCCCTG ACCTGCACCG TGTCCGGCGG CTCCCTGTCC TCCAGCTTCT CCTACTGGGT CTGGATCCGG CAGCCCCCTG GCAAGGGCCT GGAATGGATC GGCACCATCT ACTACTCCGG CAACACCTAC TACAACCCCA GCCTGAAGTC CCGGCTGACC ATCTCCGTGG ACACCTCCAA GAACCACTTC AGCCTGAAGC TGTCCTCCGT GACCGCCGCT GACACCGCCG TGTACTACTG TGCCAGAAGG GCCGGCATCC TGACCGGCTA CCTGGACTCT TGGGGCCAGG GCACCCTGGT GACAGTGTCC TCC | 15 | TCTTACGTGC TGACCCAGTC CCCCTCCGTG TCCGTGGCTC CTGGCCAGAC CGCCAGAATC ACCTGTGGCG GCAACAACAT CGGCTCCAAG TCCGTGCACT GGTATCAGCA GAAGCCCGGC CAGGCCCCCG TGCTGGTGGT GTACGACGAC TCCGACCGGC CCTCTGGCAT CCCTGAGCGG TTCTCCGCCT CCAACTCCGG CAACACCGCC ACCCTGACCA TCTCCAGAGT GGAAGCCGGC GACGAGGCCG ACTACTACTG CCAAGTGTGG GACTCCTCCT CCGACCACGT GGTGTTCGGC GGAGGCACCA AGCTGACCGT GCTGGGCCAG CCTAAGGCCG CTCCCTCCGT GACCCTG |
| HL161C | 7 | CAGGTGCAGC TCGTGCAGTC CGGCGCAGAG GTCAAAAAGC CTGGTGCATC TGTGAAAGTG AGTTGCAAGG CTAGCGGCTA CACCTTTACC GGATGTTATA TGCATTGGGT ACGCCAAGCC CCCGGACAAG GCTTGGAATG GATGGGGCGT ATCAACCCAA ACTCTGGCGG GACTAATTAC GCCCAGAAGT TTCAGGGAAG GGTGACTATG ACAAGGGACA CATCCATATC CACCGCTTAT ATGGACCTGT CTCGACTGCG GTCTGATGAT ACAGCCGTTT ATTACTGCGC CAGAGACTAC AGCGGATGGA GCTTCGATTA TTGGGGGCAG GGTACTTTGG TCACAGTTTC AAGT | 17 | GACATCCAGA TGACCCAGTC ACCATCATCC CTTTCCGCAT CTGTCGGAGA TAGAGTGACT ATCACCTGCA GGGCTTCTCA AGGTATTTCC AACTACCTCG CCTGGTTCCA GCAAAAGCCA GGTAAAGCCC CAAAGAGCTT GATCTACGCC GCTTCTAGTC TGCAGAGTGG AGTTCCTAGT AAGTTCTCCG GCTCTGGCAG TGGCACAGAT TTTACCTTGA CCATTTCCAG CCTGCAGTCT GAGGATTTCG CTACCTACTA TTGTCAGCAG TATGACAGCT ATCCCCCCAC ATTTGGGGGG GGCACTAAGG TGGAGATAAA ACGGACAGTG GCTGCCCCTT CTGTCTTTAT T |
| HL161D | 9 | CAGCTGCAGT TGCAGGAGTC AGGCCCCGGT TTGGTTAAGC CTTCTGAAAC CCTTTCTCTC ACATGCACAG TATCCGGTGG CTCCATCTCC AGTTCAAGTT | 19 | AGCTATGAGC TGACCCAGCC TCTGAGCGTA TCTGTCGCTC TCGGCCAGAC AGCCAGAATT ACCTGTGGCG GCAATAACAT AGGATCCAAA AATGTTCACT |

TABLE 1-continued

Polynucleotide sequences of heavy-chain and light-chain variable domains of selected human FcRn antibodies

| Antibody name | Heavy-chain variable domain sequence SEQ ID NO. | Polynucleotide sequence | Light-chain variable domain sequence SEQ ID NO. | Polynucleotide sequence |
|---|---|---|---|---|
| | | ACTACTGGGG ATGGATCCGG CAACCCCCAG GAAAAGGGCT GGAGTGGATT GGCAATATAT ATTACTCTGG GTCCACCTAT TACAACCCTT CCCTGATGAG TAGAGTGACC ATCAGCGTGG ACACAAGCAA AAACCAATTC AGCCTGAAGC TTTCTAGCGT GACCGCTGCC GACACAGCTG TCTATTACTG TGCCCGCCAG CTTAGTTATA ACTGGAATGA TAGGCTGTTT GATTACTGGG GCCAGGGGAC TCTCGTTACA GTCAGCAGC | | GGTATCAGCA AAAACCTGGC CAAGCTCCCG TGCTCGTGAT CTACCGGGAC TCTAACCGAC CCAGTGGAAT CCCCGAACGC TTTAGCGGTT CCAACTCTGG AAATACAGCT ACTCTGACTA TCTCCAGGGC TCAGGCCGGG GATGAGGCCG ATTACTACTG CCAGGTGTGG GACTCAAGCA CAGTGGTCTT CGGCGGAGGT ACCAAGTTGA CTGTTCTTGG GCAGCCAAAG GCCGCACCTT CAGTGACCCT G |

TABLE 2

Amino acid sequences of heavy-chain and light-chain variable domains of selected human FcRn antibodies

| Antibody name | Heavy-chain variable domain sequence SEQ ID NO. | Amino acid sequence | Light-chain variable domain sequence SEQ ID NO. | Amino acid sequence |
|---|---|---|---|---|
| HL161A | 2 | EVQLLESGGG LVQPGGSLRL SCAASEFTFG SCVMTWVRQA PGKGLEKVSV ISGSGGSTYY ADSVKGRFTI SRDNSKNTLY LQMNSLRAED TAVYYCAKTP WWLRSPFFDY WGQGTLVTVSS | 12 | SYVLTQPPSV SVAPGQTARI TCGGNNIGST SVHWYQQKPG QAPVLVVHDD SDRPSGIPER FSGSNSGNTA TLTISRVEAG DEADYYCQVR DSSSDHVTFG GGTKLTVTGQ PKAAPSVTL |
| HL161B | 4 | QLLLQESGPG LVKPSETLSL TCTVSGGSLS SSFSYWVNTR QPPGKGLEWT GTTYYSGNTY YNPSLKSRLT TSVDTSKNHF SLNTSSVTAA DTAVYYCARR AGTLTGYLDS WGQGTLVTVSS | 14 | SYVLTQSPSV SVAPGQTARI TCGGNNIGSK SVHWYQQKPG QAPVLVVYDD SDRPSGIPER FSASNSGNTA TLTISRVEAG DEADYYCQVW DSSSDHVVFG GGTKLTVLGQ PKAAPSVTL |
| HL161BK | 6 | QLLLQESGPG LVKPSETLSL TCTVSGGSLS SSFSYWVWTR QPPGKGLEWT GTTYYSGNTY YNPSLKSRLT TSVDTSKNHF SLKLSSVTAA DTAVYYCARR AG+LTGYLDS WGQGTLVTVSS | 16 | SYVLTQSPSV SVAPGQTARI TCGGNNIGSK SVHWYQQKPG QAPVLVVYDD SDRPSGIPER FSASNSGNTA TLTISRVEAG DEADYYCQVW DSSSDHVVFG GGTKLTVLGQ PKAAPSVTL |
| HL161C | 8 | QVQLVQSGAE VKKPGASVKV SCKASGYTFT GCYMHWVRQA PGQGLEWMGR TNPNSGGTNY AQKFQGRVTM TRDTSTSTAY MDLSRLRSDD TAVYYCARDY SGWSFDYWGQ GTLVTVSS | 18 | DIQMTQSPSS LSASVGDRVT ITCRASQGIS NYLAWFQQKP GKAPKSLIYA ASSLQSGVPS KFSGSGSGTD FTLTISSLQS EDFATYYCQQ YDSYPPTFGG GTKVEIKRTV AAPSVFI |
| HL161D | 10 | QLQLQESGPG LVKPSETLSL TCTVSGGSTS SSSYYWGWTR QPPGKGLEWT GNTYYSGSTY YNPSLMSRVT TSVDTSKNQF SLKLSSVTAA DTAVYYCARQ LSYNWNDRLF DYWGQGTLVT VSS | 20 | SYELTQPLSV SVALGQTARI TCGGNNIGSK NVHWYQQKPG QAPVLVIYRD SNRPSGIPER FSGSNSGNTA TLTISRAQAG DEADYYCQVW DSSTVVFGGG TKLTVLGQPK AAPSVTL |

TABLE 3

CDR sequences of heavy-chain and light-chain variable domains of selected human FcRn antibodies

| Antibody | Heavy-chain variable domain CDR | | | Light-chain variable domain CDR | | |
|---|---|---|---|---|---|---|
| | CDR1 | CDR2 | CDR3 | CDR1 | CDR2 | CDR3 |
| SEQ ID NO. | 21 | 22 | 23 | 24 | 25 | 26 |
| HL161A | SCVMT | VISGSGGS TYYADSVKG | TPWWLRSP FFDY | GGNNIGST SVH | DDSDRPS | VRDSSSDH VI |
| SEQ ID NO. | 27 | 28 | 29 | 30 | 31 | 32 |
| HL161B (HL161BK) | FSYWV | TIYYSGNT YYNPSLKS | RAGILTGY LDS | GGNNIGSK SVH | DDSDRPS | QVWDSSSD HVV |
| SEQ ID NO. | 33 | 34 | 35 | 36 | 37 | 38 |
| | GCYMH | RINPNSGG TNYAQKFQ G | DYSGWSFDY | RASQGISN YLA | AASSLQS | QQYDSYPP TF |
| SEQ ID NO. | 39 | 40 | 41 | 42 | 43 | 44 |
| HL161D | SYYWG | NIYYSGST YYNPSLMS | QLSYNWND RLFDY | GGNNIGSK NVH | RDSNRPS | QVWDSSTV V |

Example 4

Measurement of Antigen Binding Affinity of HL161A/HL161B/HL161C/HL161D Antibodies by SPR The binding affinities of HL161A, HL161B, HL161C and HL161D antibodies by SPR were measured by immobilizing water-soluble hFcRn as a ligand onto a Protean GLC chip (Bio-Rad) and measuring the affinity. Kinetic analysis was performed using a Protean XPR36 system. shFcRn was immobilized on a GLC chip, and an antibody sample was allowed to react at a concentration of 5, and sensogram results were obtained. In kinetic analysis, a 1:1 Langmuir binding model was used, the analysis was repeated six times at each of pH 6.0 and pH 7.4, and the mean KD value was calculated. Following the immobilization step, the chip was activated under the conditions of EDAC/NHS 0.5×, 30 µL/min and 300 sec. For immobilization, shFcRn was diluted in acetate buffer (pH 5.5) to concentrations of 2 µg/mL and 250 µL and the dilution was allowed to flow on the chip at a rate of 30 µL/min. When an immobilization level of 200-300 RU was reached, the reaction was stopped. Then, deactivation was performed using ethanolamine at a rate of 30 µL/min for 300 sec. Each of the HL161 antibodies was serially 2-fold diluted from a concentration of 10 nM to 5 nM, 2.5 nM, 1.25 nM, 0.625 nM, 0.312 nM, etc., thereby preparing samples. Sample dilution was performed using 1× PBST (pH 7.4) or 1× PBST (pH 6.0) at each pH. For sample analysis, association was performed at 30 µL/min for 200 sec, and the dissociation step was performed at 50 µL/min for 600 sec, after which regeneration was performed using glycine buffer (pH 2.5) at 100 µL/min for 18 sec. The kinetic analysis of each sample was repeated six times, and then the mean antigen binding affinity (KB) was measured. The kinetic parameters of the antibodies, which resulted from the SPR analysis, are shown in Table 4 below (FIGS. 2A through 2H).

TABLE 4

Results of kinetic analysis of antibody by human FcRn-immobilized SPR

| | pH 6.0 | | | pH 7.4 | | |
|---|---|---|---|---|---|---|
| Antibody | $k_{on}$ (M$^{-1}$s$^{-1}$) | $K_{off}$ (s$^{-1}$) | $K_D$ (M) | $k_{on}$ (M$^{-1}$s$^{-1}$) | $k_{off}$ (s$^{-1}$) | $K_D$ (M) |
| HL161A | $1.81 \times 10^6$ | $3.26 \times 10^{-4}$ | $1.80 \times 10^{-10}$ | $1.32 \times 10^6$ | $3.27 \times 10^{-4}$ | $2.47 \times 10^{-10}$ |
| HL161B | $9.12 \times 10^5$ | $7.35 \times 10^{-4}$ | $8.07 \times 10^{-10}$ | $7.10 \times 10^5$ | $1.25 \times 10^{-3}$ | $1.76 \times 10^{-9}$ |
| HL161C | $1.74 \times 10^6$ | $3.32 \times 10^{-4}$ | $1.91 \times 10^{-10}$ | $1.36 \times 10^6$ | $3.16 \times 10^{-4}$ | $2.32 \times 10^{-10}$ |
| HL161D | $9.70 \times 10^5$ | $1.38 \times 10^{-3}$ | $1.43 \times 10^{-9}$ | $6.99 \times 10^5$ | $1.24 \times 10^{-3}$ | $1.78 \times 10^{-9}$ |
| hIgG$_1$ | $3.2 \times 10^5$ | $4.6 \times 10^{-4}$ | $1.4 \times 10^{-9}$ | No binding | No binding | No binding |

Example 5

Analysis of Binding of HL161A/HL161B Antibodies to Human FcRn by FACS

Figure 3:
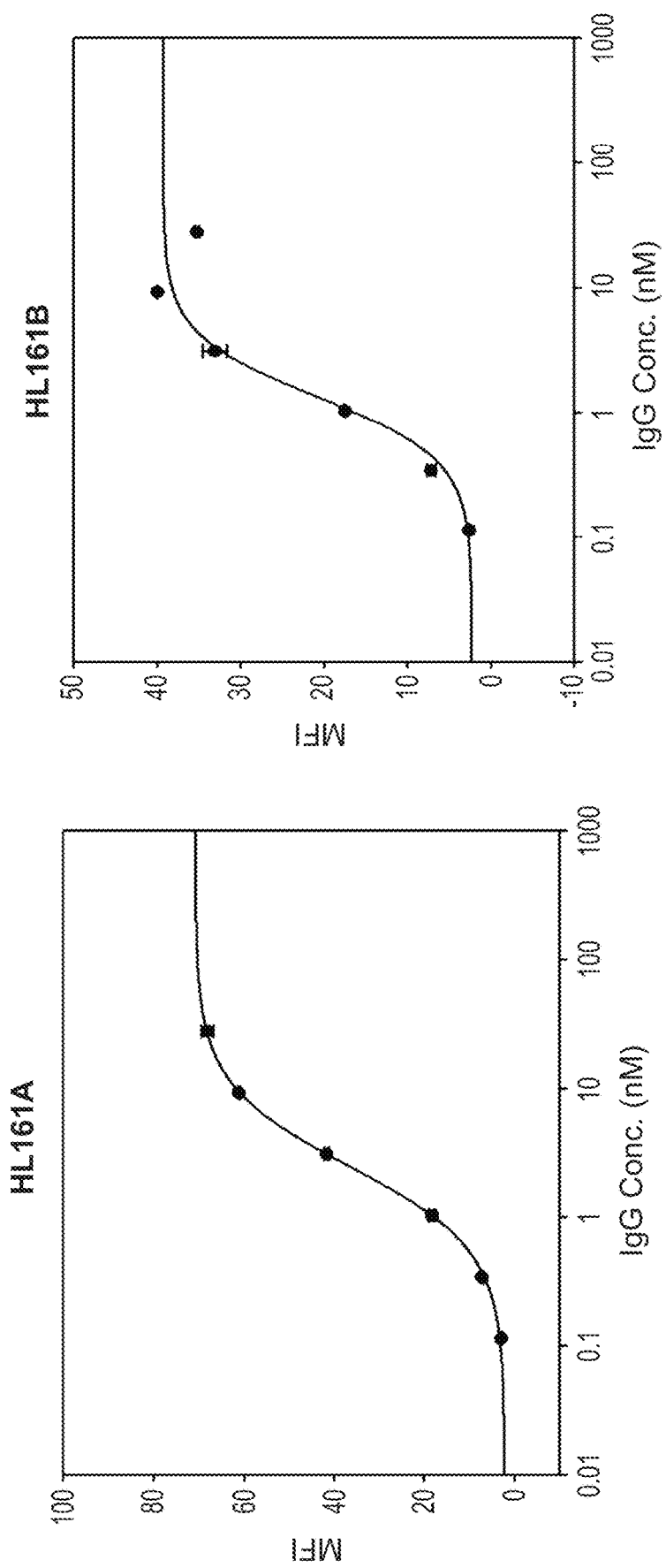
FIG. 3 shows the ability of two selected antibodies to bind to the cell surface, and shows, the results obtained by treating human FcRn-overexpressing HEK293 cells with selected HL161A and HL161B antibodies binding to human FcRn present on the cell surface and analyzing the antibodies binding to cell surface at pH 6.0 and pH 7.4. The binding of each of the HL161A and HL161B antibodies to human FcRn was expressed as an MFI value obtained by performing fluorescent activated cell sorter (FACS) using Alexa488-labelled anti-human goat antibody after treating cells with each antibody at varying pHs.

Using human FcRn-expressing stable HEK293 cells, binding to FcRn at each pH was analyzed using a FACS system. The FcRn binding test using FACS was performed in reaction buffer at pH 6.0 and pH 7.4. Specifically, 100,000 human FcRn-expressing stable HEK293 cells were washed with PBS buffer and centrifuged in a table microcentrifuge at 4500 rpm for 5 minutes to obtain cell pellets. The antibody was added to 100 µl of pH 6.0 or pH 7.4 PBS/10 mM EDTA. The remaining cells pellets were suspended in reaction buffer, and cell counting was performed 10 μL of the cell suspension was added to a slide, and the number of the cells in the cell suspension was counted in a TC10 system, after which the cell suspension was diluted with reaction buffer to a cell concentration of 2×10$^6$ cells/mL. Each antibody sample was diluted to 500 nM. For analysis at pH 6.0, the dilution was diluted to 20 nM in a 96-well v-bottom plate, and 50 μL of the dilution was added to each well. For analysis at pH 7.4, 500 nM antibody sample was diluted by 3-fold serial dilution, and analyzed at a concentration ranging from 250 nM to 0.11 nM. 50 μL of the cells diluted to 2×10$^6$ cells/mL were added to each well and suspended. The plate was mounted in a rotator at 4° C. and rotated at an angle of 15° and 10 rpm for 90 minutes. After completion of the reaction, the plate was taken out of the rotator and centrifuged at 2000 rpm for 10 minutes, and the supernatant was removed. A488 anti-hIgG goat antibody was diluted at 1:200 in reaction buffer, and 100 μL of the antibody dilution was added to each well and suspended. Next, the plate was mounted again in a rotator at 4° C. and rotated at an angle of 15° and 10 rpm for 90 minutes. After completion of the reaction, the plate was taken out of the rotator and centrifuged at 2000 rpm for 10 minutes, and the supernatant was removed. After the washing procedure was performed once more, 100 μL of reaction buffer was added to each well to dissolve the cell pellets, and the plate was transferred into a blue test tube. Next, 200 μL of reaction buffer was added to each well, and then measurement was performed in FACS. The FACS measurement was performed under the following conditions: FS 108 volts, SS 426 volts, FL1 324 volts, FL2 300 volts. These cells were analyzed by FACS using BD FACSDiva™ v6.1.3 software (BD Bioscience). The results were expressed as Mean Fluorescence Intensity (MFI) (FIG. 3). The HL161A and HL161B antibodies showed MFI values of 10.59 and 8.34, respectively, at a concentration of 10 nM and pH 6.0. At pH 7.4 and a concentration of 0.11-250 nM, the antibodies showed EC50 (Effective Concentration 50%) values of 2.46 nM and 1.20 nM, respectively, as analyzed by 4 parameter logistic regression using the MFI values.

Example 6

Analysis of Blocking Effects of HL161A/HL161B Antibodies by FACS

HEK293 cells that express hFcRn on the cell surface were treated with the two antibodies analyzed for their binding affinity for cell surface human EcRn, and the blocking effects of the antibodies were examined based on a reduction in the binding of Alexa-Fluo-488-labelled hIgG1. The analysis procedure was performed in the following manner.

2 mL of 1×TE was added to each type of naïve HEK293 cells and human FcRn-overexpressing stable HEK293 cells, which were incubated in a 5% CO$_2$ incubator at 37° C. for 1 min. The cells were recovered from the flasks, and 8 mL of reaction buffer (pH 6.0) was added thereto, after which the cells were transferred into a 50 mL conical tube. The cell suspension was centrifuged at 2000 rpm for 5 minutes to remove the supernatant, and 1 mL of reaction buffer (pH 6.0) was added to each cell pellet. Then, the cell suspension was transferred into a fresh 1.5 Eppendorf tube. Next, the cell suspension was centrifuged at 4000 rpm for 5 minutes, and the supernatant was removed. Then, reaction buffer (pH 6.0) was added to the remaining cell pellet, and the cell number of the cell suspension was counted. Finally, the cell suspension was diluted with reaction buffer to a cell concentration of 2.5×10$^6$ cells/mL.

Each antibody sample was diluted to 400 nM, and then diluted by 4-fold serial dilution in a 96-well v-bottom plate. 50 μL of the sample diluted to a final concentration of 200 nM to 0.01 nM was added to each well. Then, 10 μL of Alex488-hIgG1 diluted with 1 μM reaction buffer (pH 6.0) was each well. Finally, 40 of cells diluted to a cell concentration of 2.5×10$^6$ cells/mL were added to each well and suspended. The plate was mounted in a rotator at 4° C. and rotated at an angle of 15° and 10 rpm for 90 minutes. After completion of the reaction, the plate was taken out of the rotator, and centrifuged at 2000 rpm 10 minutes to remove the supernatant. 100 μL of reaction buffer was added to each well to dissolve the cell pellets, and the plate was transferred into a blue test tube. Then, 200 μL of reaction buffer was added to each well, and measurement was performed in FACS. The FACS measurement was performed under the following conditions: FS 108 volts, SS 426 volts, FL1 324 volts, FL2 300 volts. These cells were analyzed by FACS using BD FACSDiva™ v6.1.3 software (BD Bioscience). The results were expressed as mean fluorescence intensity (MFI). The MFI of the test group was processed after subtracting the measured MFI value of the cells alone (background signal). The percentage of the MFI of the competitor-containing tube relative to 100% of a control tube (Alexa Fluor 488 alone, and no competitor) was calculated.

$$\text{Blocking (\%)} \infty \left\{ \frac{MFI \text{ of } hFcRn \text{ stable (Competitor} + A488\text{-}hIgG1) - MFI \text{ of } HEK293 (A488\text{-}hIgG1)}{MFI \text{ of } hFcRn \text{ stable } (A488\text{-}hIgG1) - MFI \text{ of } HEK293 (A488\text{-}hIgG1)} \right\} \times 100$$

When the MFI was lower than the MFI of the human IgG1 competitor-containing tube, the competitor antibody was determined to have high competition rate. Based on the measured blocking effects (%) of the HL161A and HL161B antibodies under the conditions of pH 6.0 and concentration of 0.01-200 nM, 4-parameter logistic regression was performed. As a result, it was shown that the HL161A and HL161B antibodies showed IC50 (Inhibitory Concentration 50%) values of 0.92 nM and 2.24 nM, respectively (FIG. 4).

Example 7

Test for Effects of HL161A/HL161B in mFcRn−/−hFCRN Transgenic 32 (Tg32) Mice

Human IgG was injected into human FcRn-expressing Tg32 (hFcRn+/+, hβ2m+/+, mFcRn−/−, mβ2m−/−) mice (Jackson Laboratory), and then HL161A and HL161B together with human IgG were administered to the mice in order to examine whether the antibodies would influence the catabolism of human IgG.

HL161A and HL161B antibodies and human IgG (Greencross, IVglobulinS) were dispensed for 4-day administration at dose of 5, 10 and 20 mg/kg and stored, and PBS (phosphate buffered saline) buffer (pH 7.4) was used as a vehicle and a 20 mg/kg IgG1 control. Human FcRn Tg32 mice were adapted for about 7 days and given water and feed ad libitum. Temperature (23±2° C.), humidity (55±5%) and 12-hr-light/12-hr-dark cycles were automatically controlled. Each animal group consisted of 4 mice. To use human IgG as a tracer, biotin-conjugated hIgG was prepared using a kit (Pierce, Cat #21327). At 0 hour, 5 mg/kg of biotin-hIgG and 495 mg/kg of human IgG were administered intraperitoneally to saturate IgG in vivo. At 24, 48, 72 and 96 hours after administration of biotin-IgG, each drug was injected intraperitoneally at doses of 5, 10 and 20 mg/kg once a day. For blood collection, the mice were lightly anesthetized with Isoflurane (JW Pharmaceutical), and then blood was collected from the retro-orbtal plexus using a heparinized Micro-hematocrit capillary tube (Fisher) at 24, 48, 72, 96, 120 and 168 hours after administration of biotin-IgG. At 24, 48, 72 and 96 hours, the drug was administered after blood collection. Immediately after 0.1 mL of whole blood was received in an Eppendorf tube, plasma was separated by centrifugation and stored in a deep freezer (Thermo) at −70° C. until analysis.

The level of biotin-hIgG1 in the collected blood was analyzed by ELISA in the following manner. 100 μL of Neutravidin (Pierce, 31000) was added to a 96-well plate (Costar, Cat. No: 2592) to a concentration of 1.0 μg/ml, and then coated at 4° C. for 16 hours. The plate was washed three times with buffer A (0.05% Tween-20, 10 mM PBS, pH 7.4), and then incubated in 1% BSA-containing PBS (pH 7.4) buffer at room temperature for 2 hours. Next, the plate was washed three times with buffer A, and then a Neutravidin plate was prepared with 0.5% BSA-containing PBS (pH 7.4) buffer so as to correspond to 1 μg/ml. A blood sample was serially diluted 500-1000-fold in buffer B (100 mM MES, 150 mM NaCl, 0.5% BSA IgG-free, 0.05% Tween-20, pH 6.0), and 150 μl of the dilution was added to each well of the plate. The added sample was allowed to react at room temperature for 1 hour. Next, the plate was washed three times with buffer A, and then 200 μl of 1 nM HRP-conjugated anti-human IgG goat antibody was added to each well and incubated at 37° C. for 2 hours. Next, the plate was washed three times with ice cold buffer B, and then 100 μl of the substrate solution tetramethylbenzidine (RnD, Cat. No: DY999) was added to each well and allowed to react at room temperature for 15 minutes. 50 μl of 1.0 M sulfuric acid solution (Samchun, Cat. No: S2129) was added to each well to stop the reaction, after which the absorbance at 450 nm was measured.

Figure 5A:
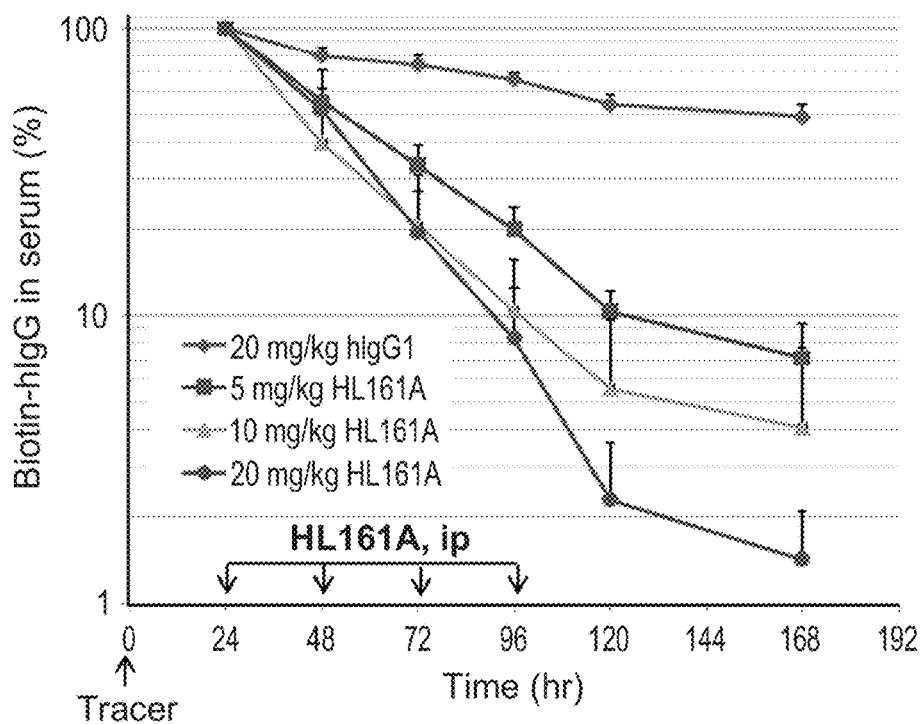
FIGS. 5A and 5B show the results of analyzing the effects of HL161A and HL161B antibodies, selected from human FcRn-expressing transgenic mouse Tg32 (hFcRn+/+, hβ2m+/+, mFcRn−/−, mβ2m−/−), on the catabolism of hIgG1. At 0 hour, 5 mg/kg of biotin-hIgG and 495 mg/kg of human IgG were intraperitoneally administered to saturate IgG in vivo. Regarding drug administration, at 24, 48, 72 and 96 hours after administration of biotin-IgG, IgG1, HL161A, HL161B or PBS was injected intraperitoneally at doses of 5, 10 and 20 mg/kg once a day. Sample collection was performed at 24, 48, 72, 96, 120 and 168 hours after administration of biotin-IgG. At 24, 48, 72 and 96 hours, blood was collected before drug administration, and the remaining amount of biotin-IgG was analyzed by an ELISA method. The results were expressed as the ratio of the remaining amount at each time point to 100% for the remaining amount in the blood sample collected at 24 hours.
Figure 5B:
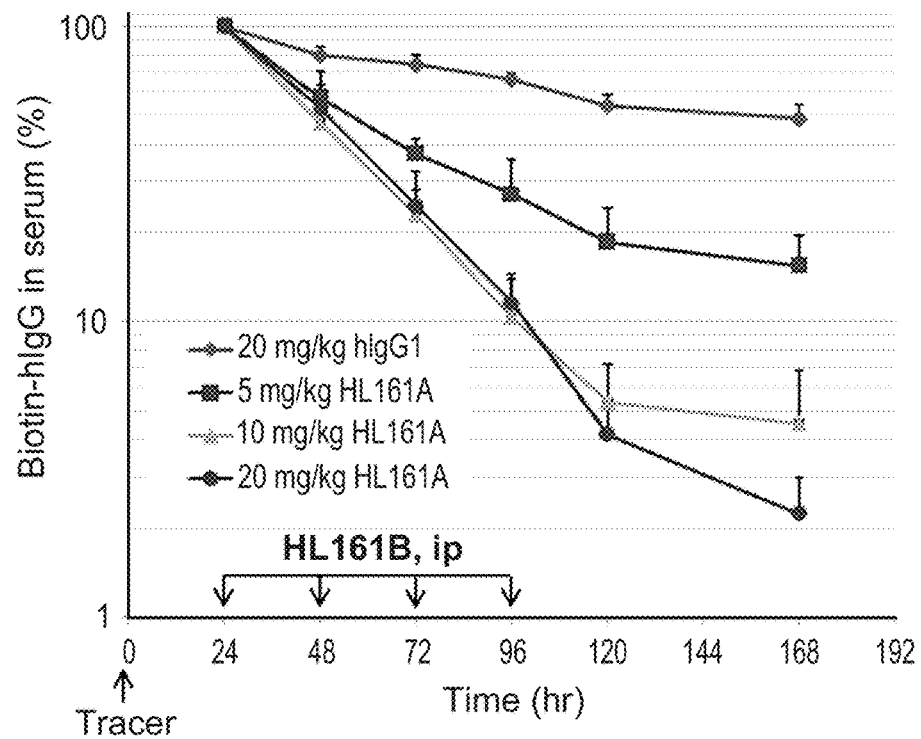

The concentration of biotin-IgG after 24 hours (approximately Tmax of biotin-IgG in mice; before the occurrence of catabolism of biotin-IgG) was set at 100%, and the percentages of the concentration at other time points relative to the concentration at 24 hours were analyzed. The results of the analysis indicated that the half-lives of the vehicle and the 20 mg/kg IgG1 control were 103 hours and 118 hours, respectively. However, the blood IgG half-life of the HL161A antibody, which showed excellent human FcRn binding affinity and blocking effect in the in vitro analysis and the fastest IgG catabolism in the human FcRn transgenic Tg32 mice, were 30, 23 and 18 hours at varying doses. In addition, the HL161B antibody showed. IgG half-lives of 41, 22 and 21 hours. This suggests that the pH-independent and Fc-non-competitive antibodies for hFcRn have the effect of increasing the catabolism of endogenous antibodies (FIGS. 5A and 5B).

Example 8

Test for Effects of HL161A/HL161B in Monkeys

Using cynomolgus monkeys having a homology of 96% to human FcRn, the monkey IgG, IgA, IgM and albumin levels by administration of the HL161A and HL161B antibodies were analyzed, and the pharmacokinetics (PK) profiles of the antibodies were analyzed.

1) Analysis of Change in Expression of Immunoglobulin G in Monkey Blood

Figure 6B:
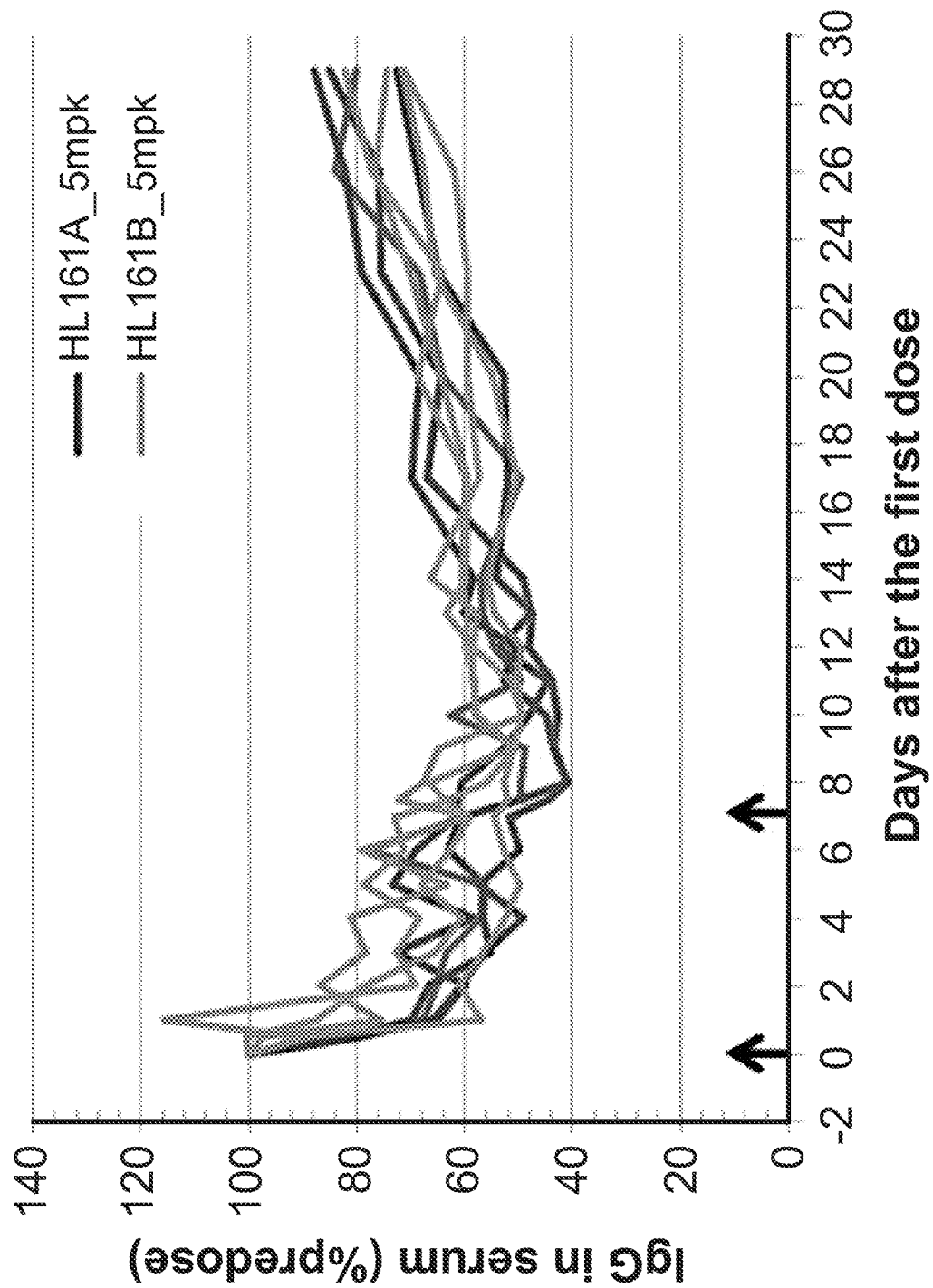
Figure 6C:
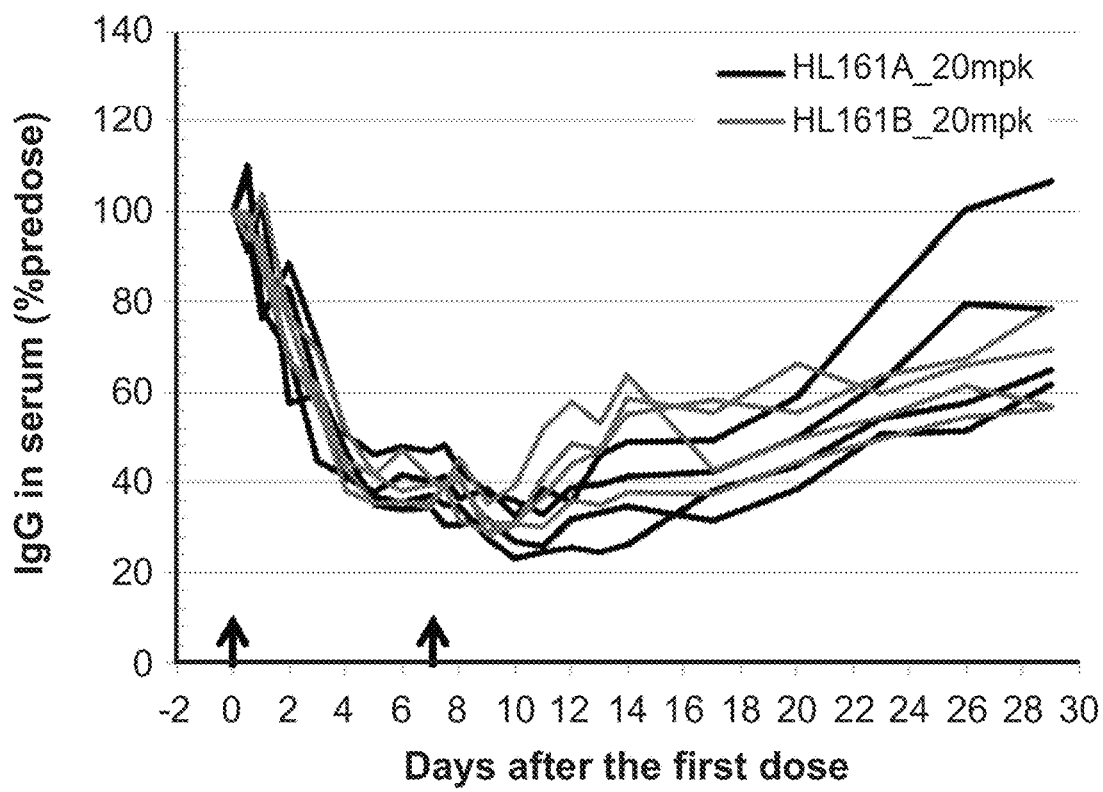

First, a change in monkey IgG was measured by ELISA analysis. 100 μL of anti-human IgG Fc antibody (BethylLab, A80-104A) was loaded into each well of a 96-well plate (Costar, Cat. No: 2592) to a concentration of 4.0 μg/mL, and then coated at 4° C. for 16 hours. The plate was washed three times with washing buffer (0.05% Tween-20, 10 mM PBS, pH 7.4), and then incubated with 1% BSA-containing PBS (pH7.4) buffer at room temperature for 2 hours. The standard monkey IgG was used at a concentration of 3.9-500 ng/mL, and the blood sample was diluted 80,000-fold in 1% BSA-containing PBS (pH7.4) buffer, and the dilution was loaded into the plate and incubated at room temperature for 2 hours. Next, the plate was washed three times with washing buffer, and then 100 μL of a 20,000-fold dilution of anti-hIgG antibody (Biorad, 201005) was loaded into the plate and allowed to react at room temperature for hour. After each plate was washed, 100 μL of the substrate solution 3,3',5, 5'-tetramethylbenzidine (RnD, Cat. No: DY999) was loaded into the plate and allowed to react at room temperature for minutes, after which 50 μL of 1.0 M sulfuric acid solution (Samchun, Cat. No: S2129) was added to each well to stop the reaction. For analysis, absorbance (CD) was measured using a 450 nm and 540 nm absorbance reader (MD, Model: VersaMax). As a result, it was shown that, when each of the HL161A and HL161B antibodies was administered intravenously into cynomolgus monkey at doses of 5 and 20 mg/kg once a week, the monkey IgG level decreased in a dose-dependent manner, and the HL161 antibodies effectively blocked the IgG-FcRn interaction. 5 mg/kg of HL161A reduced the monkey IgG level to 47.1% on day 9, and 20 mg/kg of HL161A reduced the monkey IgG level to 29.6% on day 10. 5 mg/kg of HL161B reduced the monkey IgG level to 53.6% on day 10, and 20 mg/kg of HL161B reduced the monkey IgG level to 31% on day 9, suggesting that the two antibodies showed similar results (Table 5 and FIGS. 6A through 6C). In addition, the change in monkey IgG level by intravenous administration of HL161A and HL161B was compared between individuals, and as a result, it was shown that the monkey IgG level was decreased between individuals in a very similar way.

TABLE 5

Change (%) in monkey IgG level by administration of HL161A and HL161B

|  |  | HL161A | | HL161B | |
| --- | --- | --- | --- | --- | --- |
| Day | Vehicle | 5 mg/kg | 20 mg/kg | 5 mg/kg | 20 mg/kg |
| 0 day | 100.0 ± 0.0 | 100.0 ± 0.0 | 100.0 ± 0.0 | 100.0 ± 0.0 | 100.0 ± 0.0 |
| 0.5 day | 99.0 ± 4.8 | 81.5 ± 1.8 | 101.5 ± 9.0 | 94.3 ± 5.4 | 96.2 ± 3.0 |

TABLE 5-continued

Change (%) in monkey IgG level by administration of HL161A and HL161B

| | | HL161A | | HL161B | |
|---|---|---|---|---|---|
| Day | Vehicle | 5 mg/kg | 20 mg/kg | 5 mg/kg | 20 mg/kg |
| 1 day | 97.6 ± 15.9 | 67.2 ± 2.0 | 86.2 ± 11.9 | 83.9 ± 24.7 | 94.1 ± 7.0 |
| 2 day | 97.8 ± 6.2 | 63.0 ± 3.3 | 74.2 ± 14 | 73.7 ± 11.3 | 71.7 ± 5.4 |
| 3 day | 104.5 ± 13.1 | 61.8 ± 8.0 | 59.2 ± 11.0 | 68.3 ± 9.3 | 61.3 ± 6.0 |
| 4 day | 100.9 ± 16.7 | 55.3 ± 4.1 | 45.1 ± 4.6 | 65.5 ± 12.2 | 44.3 ± 5.6 |
| 5 day | 103.4 ± 12.5 | 60.8 ± 8.3 | 38.8 ± 4.9 | 65.0 ± 11.9 | 38.4 ± 3.7 |
| 6 day | 113.3 ± 8.5 | 64.9 ± 11.7 | 39.7 ± 6.4 | 66.4 ± 11.3 | 39.0 ± 5.4 |
| 7 day | 116.9 ± 23.3 | 58.7 ± 4.7 | 39.6 ± 5.4 | 61.4 ± 8.0 | 37.5 ± 3.2 |
| 7.5 day | 92.4 ± 10.4 | 51.2 ± 7.2 | 38.7 ± 7.8 | 62.8 ± 8.3 | 39.3 ± 0.4 |
| 8 day | 94.6 ± 8.7 | 48.0 ± 9.3 | 36.1 ± 5.3 | 60.7 ± 7.5 | 39.6 ± 5.9 |
| 9 day | 117.6 ± 14.3 | 47.1 ± 4.4 | 33.8 ± 5.0 | 54.3 ± 6.9 | 31.0 ± 3.1 |
| 10 day | 115.1 ± 16.7 | 49.7 ± 8.9 | 29.6 ± 5.8 | 53.6 ± 4.9 | 32.8 ± 4.3 |
| 11 day | 114.6 ± 18.9 | 47.7 ± 4.2 | 30.4 ± 6.5 | 54.7 ± 4.2 | 39.9 ± 9.1 |
| 12 day | 109.5 ± 13.1 | 51.7 ± 3.1 | 32.9 ± 5.7 | 56.5 ± 4.7 | 46.7 ± 9.1 |
| 13 day | 111.1 ± 21.2 | 52.9 ± 6.4 | 35.7 ± 9.2 | 58.7 ± 3.8 | 45.4 ± 7.6 |
| 14 day | 128.9 ± 17.7 | 54.7 ± 4.2 | 37.8 ± 9.6 | 60.6 ± 4.2 | 53.8 ± 11.3 |
| 17 day | 95.6 ± 6.6 | 59.5 ± 10.3 | 40.2 ± 7.4 | 56.7 ± 4.4 | 48.4 ± 10.0 |
| 20 day | 92.5 ± 8.4 | 62.4 ± 6.7 | 47.6 ± 8.9 | 61.8 ± 6.0 | 54.0 ± 9.5 |
| 23 day | 107.1 ± 15.2 | 71.9 ± 6.5 | 61.8 ± 13.3 | 64.9 ± 4.4 | 56.8 ± 6.0 |
| 26 day | 104.0 ± 5.6 | 77.7 ± 6.8 | 72.2 ± 22.4 | 70.8 ± 7.4 | 62.4 ± 5.8 |
| 29 day | 102.4 ± 8.3 | 81.4 ± 6.7 | 77.9 ± 20.5 | 74.8 ± 5.1 | 65.4 ± 10.8 |

2) Analysis of Pharmacokinetic Profiles of HL161A/HL161B in Monkey Blood

Figure 7A:
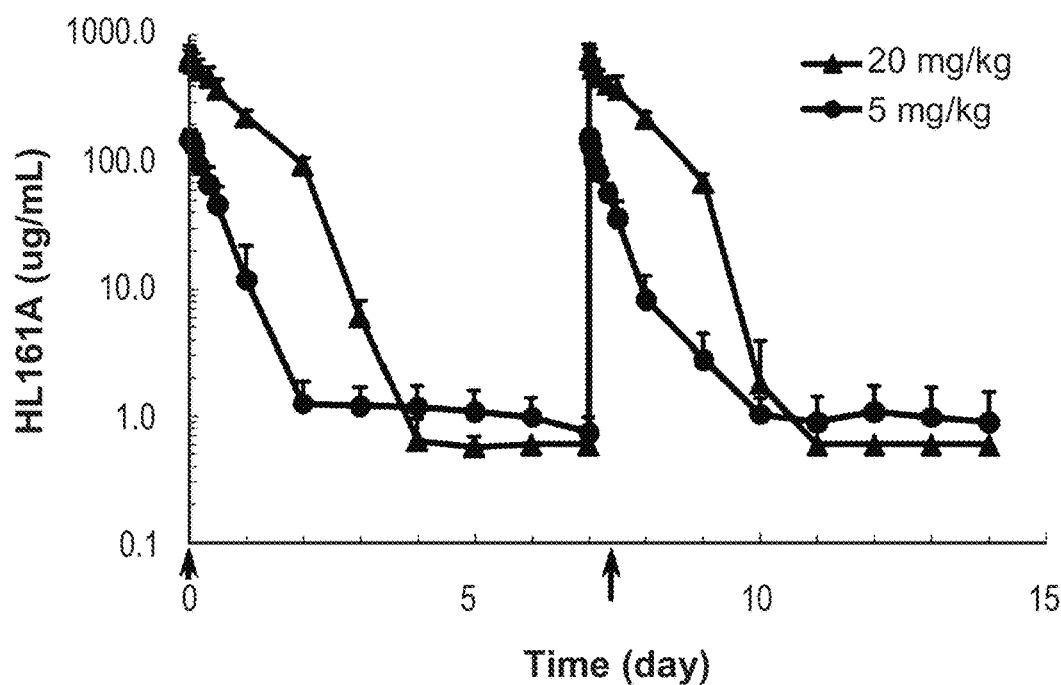

The time-dependent pharmacokinetic profiles (PK) of HL161A and HL161B after intravenous administration were analyzed by competitive ELISA. Specifically, a solution of 2 μg/mL of Neutravidin was prepared, and 100 μL of the solution was coated on each well of a 96-well plate, and then incubated at 4° C. for 18 hours. The plate was washed three time with 300 μL of wash buffer (0.05% Tween 20 containing 10 mM PBS, pH 7.4), and then each well was incubated with 1% BSA-containing PBS (pH 7.4) buffer at 25° C. for 2 hours. Biotinylated hFcRn was diluted with PBS to 1 μg/mL, and then 100 μL of the dilution was added to each well of the 96-well plate and incubated at 25° C. for 1 hour. Next, the plate was washed three times with 300 μL of wash buffer to remove unbound hFcRn, and then a standard sample (0.156-20 ng/mL) was added to each well and incubated at 25° C. for 2 hours. Next, the plate was washed three times with wash buffer, and 100 μL of a 1:10,000 dilution of detection antibody in PBS was added to each well and incubated at 25° C. for 1.5 hours. The plate was finally washed three times, and 100 μL of TME solution was added to each buffer and incubated at room temperature for 5 minutes, after which 50 μL of 1M sulfuric acid as a reaction stop solution was added to each well to stop the reaction. Next, the absorbance at 450 nm was measured with a microplate reader. The analysis results for HL161A and HL161B are shown in Table 6 below, and as can be seen therein, the pharmacokinetic profile of the antibodies increased in a dose-dependent manner. The half-life (T1/2) of the antibodies was about 6-12 days, which was shorter than that of generally known antibodies. In addition, it was shown that the half-life, when observing overall, AUC and Cmax of HL161B were higher than those of HL161A (FIGS. 7A and 7B).

TABLE 6

Analysis results for pharmacokinetic profiles of HL161A and HL161B at varying doses

| Ab (Dose) | Day | Cmax (mg/ml) | AUC (mg/ml · hr) | $T_{1/2}$ (hr) |
|---|---|---|---|---|
| HL161A (5 mg/kg) | 0-7 | 157 ± 31 | 1,601 ± 501 | 6.9 ± 0.9 |
| | 7-14 | 157 ± 25 | 1,388 ± 334 | 10.3 ± 2.8 |
| HL161A (20 mg/kg) | 0-7 | 692 ± 138 | 13,947 ± 2,459 | 9.0 ± 0.6 |
| | 7-14 | 724 ± 125 | 12,699 ± 2,114 | 7.6 ± 1.6 |
| HL161B (5 mg/kg) | 0-7 | 178 ± 56 | 2,551 ± 1,356 | 7.9 ± 1.3 |
| | 7-14 | 187 ± 9 | 2,772 ± 466 | 9.4 ± 0.5 |
| HL161B (20 mg/kg) | 0-7 | 823 ± 38 | 21,867 ± 1,088 | 11.7 ± 1.0 |
| | 7-14 | 868 ± 66 | 16,116 ± 1,501 | 6.8 ± 0.9 |

3) Analysis of Change in IgM and IgA Antibody Levels in Monkey Blood

ELISA analysis for measuring IgM and IgA levels in monkey blood was performed in a manner similar to the ELISA method for measuring IgG levels. Specifically, 100 μL of anti-monkey IgM antibody (Alpha Diagnostic, 70033) or IgA antibody (Alpha Diagnostic, 70043) was added to each well of a 96-well plate to a concentration of 2.0 μg/mL, and then coated at 4° C. for 16 hours. The plate was washed three times with wash buffer (0.05% Tween-20 containing 10 mM ABS, pH 7.4), and then incubated with 1% BSA-containing PBS (pH7.4) buffer at room temperature for 2 hours. The standard monkey IgM was analyzed at a concentration of 7.8-1,000 ng/mL, and IgA was analyzed at 15.6-2,000 ng/mL. The blood sample was diluted 10,000- or 20,000-fold in 1% BSA-containing ABS (pH7.4) buffer, and the dilution was added to each well and incubated at room temperature for 2 hours. Next, the plate was washed three times with wash buffer, and then 100 μL of a 5,000-fold dilution of each of anti-monkey IgM secondary antibody (Alpha Diagnostic, 70031) and anti-monkey IgA secondary antibody (KPL, 074-11-011) was added to each well and allowed to react at room temperature for 1 hour. The plate was finally washed three times, and 100 L of the substrate solution 3,3',5,5'-tetramethylbenzidine (RnD, Cat. No: DY999) was added to each well and allowed to react at room temperature for 7 minutes. Next, 50 μL of 1.0 M sulfur solution (Samchun, Cat. No: S2129) was added to each well to stop the reaction. The absorbance of each well was measured with a 450 and 540 nm absorbance reader (MD, Model: VersaMax).

4) Analysis of Change in Albumin Levels in Monkey Blood

The analysis of a change in albumin levels in monkey blood was performed using a commercial ELISA kit (Assaypro, Cat. No: EKA2201-1). Briefly, monkey serum as test sample was 4000-fold diluted, and 25 μL of the dilution was added to each well of a 96-well plate coated with an antibody capable of binding to monkey albumin. 25 μL of biotinylated monkey albumin solution was added to each well and incubated at 25° C. for 2 hours. The plate was washed three times with 200 μL of wash buffer, and then 50 μL of a 1:100 dilution of streptavidin-peroxidase conjugated antibody was added to each well and incubated at 25° C. for 30 minutes. The plate was finally washed three times, and then 50 μL of a substrate was added to each well and incubated at room temperature for 10 minutes. Next, 50 μL of a react on stop solution was added to each well, and the absorbance at 450 nm was measured. As a result, the clear changes in monkey IgM, IgA and albumin levels by administration of the HL161A and HL161B antibodies were not observed throughout the test period (FIGS. 8A through 8C). Thus, is concluded that the HL161 antibody is involved only in IgG levels and does not influence the levels of IgM and IgA, suggesting that it will have no significant influence on the decrease in immunity by a decrease in immunoglobulin levels. In addition, no significant change in the monkey albumin level was observed throughout the test period, suggesting that the HL161A and HL161B antibodies specifically block only the IgG-FcRn interactions.

5) Analysis of Blood Biochemical Levels and Urinary Components

Finally, blood biochemical analysis and urinary analysis by administration of the antibodies were performed using samples on day 14 of the test. Blood biochemical markers, including aspartate aminotransferase (AST), alanine aminotransferase (ALT), alkaline phosphatase (ALP), creatine phosphokinase (CPK), total bilirubin (TBIL), glucose (GLU), total cholesterol (TCHO), triglyceride (TG), total protein (TP), albumin (Alb), albumin/globulin (A/G), blood urea nitrogen (BUN), creatinine (CRE), inorganic phosphorus (IP), calcium (Ca), sodium (Na), potassium (K) and chloride (Cl), were analyzed using the Hitachi 7180 system. In addition, markers for urinary analysis, including leukocyte (LEU), nitrate (NIT), urobilinogen (URO), protein (PRO), pH, occult blood (BLC), specific gravity (SG), ketone body (KET), bilirubin (BIL), glucose (GLU), and ascorbic acid (ASC), were analyzed using the Mission U120 system. Although there were slight changes in the levels, the measured levels were included in the normal level ranges of cynomolgus monkeys.

Although the present disclosure has been described in detail with reference to the specific features, it will be apparent to those skilled in the art that this description is only for purposes of illustration and does not limit the scope of the present disclosure. Thus, the substantial scope of the present disclosure will be defined by the appended claims and equivalents thereof.

The invention claimed is:

1. An isolated anti-FcRn antibody or an antigen-binding fragment thereof comprising:
   a heavy chain variable region comprising a CDR1 comprising the amino acid sequence of SEQ ID No: 33, a CDR2 comprising the amino acid sequence of SEQ ID No: 34, and a CDR3 comprising the amino acid sequence of SEQ ID No: 35; and a light chain variable region comprising a CDR1 comprising the amino acid sequence of SEQ ID No: 36, a CDR2 comprising the amino acid sequence of SEQ ID No: 37, and a CDR3 comprising the amino acid sequence of SEQ ID No: 38; or
   (ii) a heavy chain variable region comprising a CDR1 comprising the amino acid sequence of SEQ ID No: 39, a CDR2 comprising the amino acid sequence of SEQ ID No: 40, and a CDR3 comprising the amino acid sequence of SEQ ID No: 41; and a light chain variable region comprising a CDR1 comprising the amino acid sequence of SEQ ID No: 42, a CDR2 comprising the amino acid sequence of SEQ ID No: 43, and a CDR3 comprising the amino acid sequence of SEQ ID No: 44.

2. The antibody or antigen-binding fragment of claim 1, wherein the antibody or antigen-binding fragment comprises a heavy chain variable region comprising a CDR1 comprising the amino acid sequence of SEQ ID No: 33, a CDR2 comprising the amino acid sequence of SEQ ID No: 34, and a CDR3 comprising the amino acid sequence of SEQ ID No: 35; and a light chain variable region comprising a CDR1 comprising the amino acid sequence of SEQ ID No: 36, a CDR2 comprising the amino acid sequence of SEQ ID No: 37, and a CDR3 comprising the amino acid sequence of SEQ ID No: 38.

3. The antibody or antigen-binding fragment of claim 2, wherein the antibody or antigen-binding fragment comprises a heavy chain variable region having at least 90% homology with the amino acid sequence of SEQ ID No: 8, and a light chain variable region having at least 90% homology with the amino acid sequence of SEQ ID No: 18.

4. The antibody or antigen-binding fragment of claim 3, wherein the antibody or antigen-binding fragment comprises a heavy chain variable region comprising the amino acid sequence of SEQ ID No: 8, and a light chain variable region comprising the amino acid sequence of SEQ ID No: 18.

5. The antibody or antigen-binding fragment of claim 1, wherein the antibody or antigen-binding fragment comprises a heavy chain variable region comprising a CDR1 comprising the amino acid sequence of SEQ ID No: 39, a CDR2 comprising the amino acid sequence of SEQ ID No: 40, and a CDR3 comprising the amino acid sequence of SEQ ID No: 41; and a light chain variable region comprising a CDR1 comprising the amino acid sequence of SEQ ID No: 42, a CDR2 comprising the amino acid sequence of SEQ ID No: 43, and a CDR3 comprising the amino acid sequence of SEQ ID No: 44.

6. The antibody or antigen-binding fragment of claim 5, wherein the antibody or antigen-binding fragment comprises a heavy chain variable region having at least 90% homology with the amino acid sequence of SEQ ID No: 10, and a light chain variable region having at least 90% homology with the amino acid sequence of SEQ ID No: 20.

7. The antibody or antigen-binding fragment of claim 6, wherein the antibody or antigen-binding fragment comprises a heavy chain variable region comprising the amino acid sequence of SEQ ID No: 10, and a light chain variable region comprising the amino acid sequence of SEQ ID No: 20.

8. The antibody or antigen-binding fragment of claim 1, wherein the antibody is a monoclonal antibody.

9. The antibody or antigen-binding fragment of claim 1, wherein the antibody is a murine antibody, chimeric antibody, humanized antibody, or human antibody.

10. The antibody or antigen-binding fragment of claim 1, wherein the antibody is a human antibody.

11. The antibody or antigen-binding fragment of claim 1, wherein the antibody or antigen-binding fragment is a full-length antibody, Fab, F(ab')2, Fv, scFv, dual-specific antibody, bibody, minibody, tribody, bispecific antibody, trispecific antibody, multi specific antibody, diabody, triabody, tetrabody, intrabody, small modular immunopharmaceutical (SMIP), or binding-domain immunoglobulin fusion protein.

12. The antibody or antigen-binding fragment of claim 1, wherein the antibody is an IgD antibody, IgE antibody, IgM antibody, IgG1 antibody, IgG2 antibody, IgG3 antibody, or IgG4 antibody.

13. The antibody or antigen-binding fragment of claim 1, wherein the antibody is an IgG1 antibody.

14. A composition comprising the antibody or antigen-binding fragment of claim 1 labelled with a detection label.

15. A polynucleotide encoding the antibody or antigen-binding fragment of claim 1.

16. The polynucleotide of claim 15, comprising a nucleic acid sequence of SEQ ID No: 7 encoding a heavy chain variable region, and a nucleic acid sequence of SEQ ID No: 17 encoding a light chain variable region.

17. The polynucleotide of claim 15, comprising a nucleic acid sequence of SEQ ID No: 9 encoding a heavy chain variable region, and a nucleic acid sequence of SEQ ID No: 19 encoding a light chain variable region.

18. A recombinant expression vector comprising the polynucleotide of claim 15.

19. A host cell transfected with the recombinant expression vector of claim 18.

20. A method of preparing an anti-FcRn antibody or an antigen-binding fragment thereof, comprising culturing the host cell of claim 19 to produce the antibody or antigen-binding fragment; and isolating and purifying the produced antibody or antigen-binding fragment.

21. A pharmaceutical composition comprising the antibody or antigen-binding fragment of claim 1 and one or more pharmaceutically acceptable carriers.

22. A method of treating a patient suffering from an autoimmune disease, comprising administering to the patient an effective amount of a pharmaceutical composition comprising the antibody or antigen-binding fragment of claim 1 and one or more pharmaceutically acceptable carriers.

23. The method of claim 22, wherein the autoimmune disease is immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa acquisita, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, lupus, idiopathic thrombocytopenic purpura, lupus nephritis, or membranous nephropathy.

* * * * *

SEQUENCE LISTING

```
<160> NUMBER OF SEQ ID NOS: 44

<210> SEQ ID NO 1
<211> LENGTH: 363
<212> TYPE: DNA
<213> ORGANISM: Artificial Sequence
<220> FEATURE:
<223> OTHER INFORMATION: Hv of HL161A

<400> SEQUENCE: 1
gaagtgcagc tgctggaatc cggcggaggc ctggtgcagc ctggcggctc tctgagactg      60
tcctgcgccg cctccgagtt caccttcggc agctgcgtga tgacctgggt ccgacaggct     120
cccggcaagg gcctggaatg ggtgtccgtg atctccggct ccggcggctc cacctactac     180
gccgactctg tgaagggccg gttcaccatc tcccgggaca actccaagaa cacctgtac      240 ctgcagatga actccctgcg ggccgaggac accgccgtgt actactgcgc caagaccccc     300
tggtggctgc ggtccccctt cttcgattac tggggccagg gcaccctggt gacagtgtcc     360
tcc                                                                    363

<210> SEQ ID NO 2
<211> LENGTH: 121
<212> TYPE: PRT
<213> ORGANISM: Artificial Sequence
<220> FEATURE:
<223> OTHER INFORMATION: Hv of HL161A

<400> SEQUENCE: 2

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Glu Phe Thr Phe Gly Ser Cys
            20                  25                  30

Val Met Thr Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Pro Trp Trp Leu Arg Ser Pro Phe Phe Asp Tyr Trp Gly
            100                 105                 110

Gln Gly Thr Leu Val Thr Val Ser Ser
        115                 120

<210> SEQ ID NO 3
<211> LENGTH: 363
<212> TYPE: DNA
<213> ORGANISM: Artificial Sequence
<220> FEATURE:
<223> OTHER INFORMATION: Hv of HL161B

<400> SEQUENCE: 3
caactgttgc tccaggaatc cggtcctggt cttgtaaagc catctgagac tctctccctt      60
acctgtaccg ttagcggagg aagtctttcc tcaagcttct cctactgggt gtggatcaga     120
cagcctcccg gaaagggtt ggagtggatt ggcacaatat actactccgg caacacttac      180
tataacccca gcctgaagag caggctgact atctctgtcg acaccagtaa aaatcacttt     240
tctctgaatc tgtcttcagt gaccgcagcc gacaccgccg tgtattattg cgctcggcgc     300
gccgggattc tgacaggcta tctggattca tggggccagg gacattggt tacagtgtct      360 agt                                                                  363

<210> SEQ ID NO 4
<211> LENGTH: 121
<212> TYPE: PRT
<213> ORGANISM: Artificial Sequence
<220> FEATURE:
<223> OTHER INFORMATION: Hv of HL161B

<400> SEQUENCE: 4

Gln Leu Leu Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Ser
            20                  25                  30

Phe Ser Tyr Trp Val Trp Ile Arg Gln Pro Pro Gly Lys Gly Leu Glu
        35                  40                  45

Trp Ile Gly Thr Ile Tyr Tyr Ser Gly Asn Thr Tyr Tyr Asn Pro Ser
    50                  55                  60

Leu Lys Ser Arg Leu Thr Ile Ser Val Asp Thr Ser Lys Asn His Phe
65                  70                  75                  80

Ser Leu Asn Leu Ser Ser Val Thr Ala Ala Asp Thr Ala Val Tyr Tyr
                85                  90                  95

Cys Ala Arg Arg Ala Gly Ile Leu Thr Gly Tyr Leu Asp Ser Trp Gly
            100                 105                 110

Gln Gly Thr Leu Val Thr Val Ser Ser
        115                 120
```

<210> SEQ ID NO 5
<211> LENGTH: 363
<212> TYPE: DNA
<213> ORGANISM: Artificial Sequence
<220> FEATURE:
<223> OTHER INFORMATION: Hv of HL161BK

<400> SEQUENCE: 5

```
cagctgctgc tgcaagaatc cggccctggc ctggtgaaac cctccgagac actgtccctg      60
acctgcaccg tgtccggcgg ctccctgtcc tccagcttct cctactgggt ctggatccgg     120 cagcccctg  gcaagggcct ggaatggatc ggcaccatct actactccgg caacacctac     180
tacaacccca gcctgaagtc ccggctgacc atctccgtgg acacctccaa gaaccacttc     240
agcctgaagc tgtcctccgt gaccgccgct gacaccgccg tgtactactg tgccagaagg     300
gccggcatcc tgaccggcta cctggactct tggggccagg gcaccctggt gacagtgtcc     360
tcc                                                                   363
```

<210> SEQ ID NO 6
<211> LENGTH: 121
<212> TYPE: PRT
<213> ORGANISM: Artificial Sequence
<220> FEATURE:
<223> OTHER INFORMATION: Hv of HL161BK

<400> SEQUENCE: 6

```
Gln Leu Leu Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Ser
            20                  25                  30

Phe Ser Tyr Trp Val Trp Ile Arg Gln Pro Pro Gly Lys Gly Leu Glu
        35                  40                  45

Trp Ile Gly Thr Ile Tyr Tyr Ser Gly Asn Thr Tyr Tyr Asn Pro Ser
    50                  55                  60

Leu Lys Ser Arg Leu Thr Ile Ser Val Asp Thr Ser Lys Asn His Phe
65                  70                  75                  80

Ser Leu Lys Leu Ser Ser Val Thr Ala Ala Asp Thr Ala Val Tyr Tyr
                85                  90                  95

Cys Ala Arg Arg Ala Gly Ile Leu Thr Gly Tyr Leu Asp Ser Trp Gly
            100                 105                 110

Gln Gly Thr Leu Val Thr Val Ser Ser
        115                 120
```

<210> SEQ ID NO 7
<211> LENGTH: 354
<212> TYPE: DNA
<213> ORGANISM: Artificial Sequence
<220> FEATURE:
<223> OTHER INFORMATION: Hv of HL161C

<400> SEQUENCE: 7

```
caggtgcagc tcgtgcagtc cggcgcagag gtcaaaaagc ctggtgcatc tgtgaaagtg      60
agttgcaagg ctagcggcta ccctttacc  ggatgttata tgcattgggt acgccaagcc     120
cccggacaag gcttggaatg gatggggcgt atcaacccaa actctggcgg gactaattac     180
gcccagaagt ttcagggaag ggtgactatg acaagggaca catccatatc caccgcttat     240
atggacctgt ctcgactgcg gtctgatgat acagccgttt attactgcgc cagagactac     300
agcggatgga gcttcgatta ttggggggcag ggtactttgg tcacagtttc aagt          354
```

<210> SEQ ID NO 8
<211> LENGTH: 118
<212> TYPE: PRT
<213> ORGANISM: Artificial Sequence
<220> FEATURE:
<223> OTHER INFORMATION: Hv of HL161C

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Cys
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Tyr Tyr Cys
                85                  90                  95

Ala Arg Asp Tyr Ser Gly Trp Ser Phe Asp Tyr Trp Gly Gln Gly Thr
            100                 105                 110

Leu Val Thr Val Ser Ser
        115

<210> SEQ ID NO 9
<211> LENGTH: 369
<212> TYPE: DNA
<213> ORGANISM: Artificial Sequence
<220> FEATURE:
<223> OTHER INFORMATION: Hv of HL161D

<400> SEQUENCE: 9
cagctgcagt tgcaggagtc aggccccggt ttggttaagc cttctgaaac cctttctctc      60
acatgcacag tatccggtgg ctccatctcc agttcaagtt actactgggg atggatccgg     120 caaccccag gaaaagggct ggagtggatt ggcaatatat attactctgg gtccacctat     180 tacaacccctt ccctgatgag tagagtgacc atcagcgtgg acacaagcaa aaaccaattc     240
agcctgaagc tttctagcgt gaccgctgcc gacacagctg tctattactg tgcccgccag     300
cttagttata actggaatga taggctgttt gattactggg ccaggggac tctcgttaca     360 gtcagcagc                                                            369

<210> SEQ ID NO 10
<211> LENGTH: 123
<212> TYPE: PRT
<213> ORGANISM: Artificial Sequence
<220> FEATURE:
<223> OTHER INFORMATION: Hv of HL161D

<400> SEQUENCE: 10

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser

```
            50                  55                  60
Leu Met Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gln Leu Ser Tyr Asn Trp Asn Asp Arg Leu Phe Asp Tyr
            100                 105                 110

Trp Gly Gln Gly Thr Leu Val Thr Val Ser Ser
            115                 120
```

<210> SEQ ID NO 11
<211> LENGTH: 357
<212> TYPE: DNA
<213> ORGANISM: Artificial Sequence
<220> FEATURE:
<223> OTHER INFORMATION: Lv of HL161A

<400> SEQUENCE: 11

```
tcttacgtgc tgacccagcc cccctccgtg tctgtggctc ctggccagac cgccagaatc    60
acctgtggcg gcaacaacat cggctccacc tccgtgcact ggtatcagca gaagcccggc   120
caggcccccg tgctggtggt gcacgacgac tccgaccggc cttctggcat ccctgagcgg   180
ttctccggct ccaactccgg caacaccgcc accctgacca tctccagagt ggaagccggc   240
gacgaggccg actactactg ccaagtgcga gactcctcct ccgaccacgt gatcttcggc   300
ggaggcacca agctgaccgt gctgggccag cctaaggccg ctcccctccgt gaccctg    357
```

<210> SEQ ID NO 12
<211> LENGTH: 119
<212> TYPE: PRT
<213> ORGANISM: Artificial Sequence
<220> FEATURE:
<223> OTHER INFORMATION: Lv of HL161A

<400> SEQUENCE: 12

```
Ser Tyr Val Leu Thr Gln Pro Pro Ser Val Ser Val Ala Pro Gly Gln
  1               5                  10                  15

Thr Ala Arg Ile Thr Cys Gly Gly Asn Asn Ile Gly Ser Thr Ser Val
             20                  25                  30

His Trp Tyr Gln Gln Lys Pro Gly Gln Ala Pro Val Leu Val Val His
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Arg Asp Ser Ser Ser Asp His
                 85                  90                  95

Val Ile Phe Gly Gly Gly Thr Lys Leu Thr Val Leu Gly Gln Pro Lys
            100                 105                 110

Ala Ala Pro Ser Val Thr Leu
            115
```

<210> SEQ ID NO 13
<211> LENGTH: 357
<212> TYPE: DNA
<213> ORGANISM: Artificial Sequence
<220> FEATURE:
<223> OTHER INFORMATION: Lv of HL161B

<400> SEQUENCE: 13

```
tcttacgtgc tgacccagtc cccctccgtg tccgtggctc ctggccagac cgccagaatc    60
acctgtggcg gcaacaacat cggctccaag tccgtgcact ggtatcagca gaagcccggc   120
caggcccccg tgctggtggt gtacgacgac tccgaccggc cctctggcat ccctgagcgg   180
ttctccgcct ccaactccgg caacaccgcc accctgacca tctccagagt ggaagccggc   240
gacgaggccg actactactg ccaagtgtgg gactcctcct ccgaccacgt ggtgttcggc   300
ggaggcacca agctgaccgt gctgggccag cctaaggccg ctccctccgt gaccctg      357
```

<210> SEQ ID NO 14
<211> LENGTH: 119
<212> TYPE: PRT
<213> ORGANISM: Artificial Sequence
<220> FEATURE:
<223> OTHER INFORMATION: Lv of HL161B

<400> SEQUENCE: 14

```
Ser Tyr Val Leu Thr Gln Ser Pro Ser Val Ser Val Ala Pro Gly Gln
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Ala Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu Gly Gln Pro Lys
                100                 105                 110

Ala Ala Pro Ser Val Thr Leu
            115
```

<210> SEQ ID NO 15
<211> LENGTH: 357
<212> TYPE: DNA
<213> ORGANISM: Artificial Sequence
<220> FEATURE:
<223> OTHER INFORMATION: Lv of HL161BK

<400> SEQUENCE: 15

```
tcttacgtgc tgacccagtc cccctccgtg tccgtggctc ctggccagac cgccagaatc    60
acctgtggcg gcaacaacat cggctccaag tccgtgcact ggtatcagca gaagcccggc   120
caggcccccg tgctggtggt gtacgacgac tccgaccggc cctctggcat ccctgagcgg   180
ttctccgcct ccaactccgg caacaccgcc accctgacca tctccagagt ggaagccggc   240
gacgaggccg actactactg ccaagtgtgg gactcctcct ccgaccacgt ggtgttcggc   300
ggaggcacca agctgaccgt gctgggccag cctaaggccg ctccctccgt gaccctg      357
```

<210> SEQ ID NO 16
<211> LENGTH: 119
<212> TYPE: PRT
<213> ORGANISM: Artificial Sequence
<220> FEATURE:
<223> OTHER INFORMATION: Lv of HL161BK

<400> SEQUENCE: 16

```
Ser Tyr Val Leu Thr Gln Ser Pro Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Ala Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu
            115

<210> SEQ ID NO 17
<211> LENGTH: 351
<212> TYPE: DNA
<213> ORGANISM: Artificial Sequence
<220> FEATURE:
<223> OTHER INFORMATION: Lv of HL161C

<400> SEQUENCE: 17
gacatccaga tgacccagtc accatcatcc ctttccgcat ctgtcggaga tagagtgact      60
atcacctgca gggcttctca aggtatttcc aactacctcg cctggttcca gcaaaagcca     120
ggtaaagccc caaagagctt gatctacgcc gcttctagtc tgcagagtgg agttcctagt     180
aagttctccg gctctggcag tggcacagat tttaccttga ccatttccag cctgcagtct     240
gaggatttcg ctacctacta ttgtcagcag tatgacagct atccccccac atttgggggg    300
ggcactaagg tggagataaa acggacagtg gctgccccct ctgtctttat t             351

<210> SEQ ID NO 18
<211> LENGTH: 117
<212> TYPE: PRT
<213> ORGANISM: Artificial Sequence
<220> FEATURE:
<223> OTHER INFORMATION: Lv of HL161C

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Asp Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile
            115
```

<210> SEQ ID NO 19
<211> LENGTH: 351
<212> TYPE: DNA
<213> ORGANISM: Artificial Sequence
<220> FEATURE:
<223> OTHER INFORMATION: Lv of HL161D

<400> SEQUENCE: 19

```
agctatgagc tgacccagcc tctgagcgta tctgtcgctc tcggccagac agccagaatt      60
acctgtggcg gcaataacat aggatccaaa aatgttcact ggtatcagca aaaacctggc     120
caagctcccg tgctcgtgat ctaccgggac tctaaccgac ccagtggaat ccccgaacgc     180
tttagcggtt ccaactctgg aaatacagct actctgacta tctccagggc tcaggccggg     240
gatgaggccg attactactg ccaggtgtgg gactcaagca cagtggtctt cggcggaggt     300
accaagttga ctgttcttgg cagccaaag gccgcacctt cagtgaccct g               351
```

<210> SEQ ID NO 20
<211> LENGTH: 117
<212> TYPE: PRT
<213> ORGANISM: Artificial Sequence
<220> FEATURE:
<223> OTHER INFORMATION: Lv of HL161D

<400> SEQUENCE: 20

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu
        115
```

<210> SEQ ID NO 21
<211> LENGTH: 5
<212> TYPE: PRT
<213> ORGANISM: Artificial Sequence
<220> FEATURE:
<223> OTHER INFORMATION: Hv CDR1 of HL161A

<400> SEQUENCE: 21

```
Ser Cys Val Met Thr
1               5
```

<210> SEQ ID NO 22
<211> LENGTH: 17
<212> TYPE: PRT
<213> ORGANISM: Artificial Sequence
<220> FEATURE:
<223> OTHER INFORMATION: Hv CDR2 of HL161A

<400> SEQUENCE: 22

Val Ile Ser Gly Ser Gly Gly Ser Thr Tyr Tyr Ala Asp Ser Val Lys
1               5                   10                  15
Gly

<210> SEQ ID NO 23
<211> LENGTH: 12
<212> TYPE: PRT
<213> ORGANISM: Artificial Sequence
<220> FEATURE:
<223> OTHER INFORMATION: Hv CDR3 of HL161A

<400> SEQUENCE: 23

Thr Pro Trp Trp Leu Arg Ser Pro Phe Phe Asp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Lv CDR1 of HL161A

<400> SEQUENCE: 24

Gly Gly Asn Asn Ile Gly Ser Thr Ser Val His
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Lv CDR2 of HL161A

<400> SEQUENCE: 25

Asp Asp Ser Asp Arg Pro Ser
1               5

<210> SEQ ID NO 26
<211> LENGTH: 10
<212> TYPE: PRT
<213> ORGANISM: Artificial Sequence
<220> FEATURE:
<223> OTHER INFORMATION: Lv CDR3 of HL161A

<400> SEQUENCE: 26

Val Arg Asp Ser Ser Ser Asp His Val Ile
1               5                   10

<210> SEQ ID NO 27
<211> LENGTH: 5
<212> TYPE: PRT
<213> ORGANISM: Artificial Sequence
<220> FEATURE:
<223> OTHER INFORMATION: Hv CDR1 of HL161B or HL161BK

<400> SEQUENCE: 27

Phe Ser Tyr Trp Val
1               5

<210> SEQ ID NO 28
<211> LENGTH: 16
<212> TYPE: PRT
<213> ORGANISM: Artificial Sequence
<220> FEATURE:
<223> OTHER INFORMATION: Hv CDR2 of HL161B or HL161BK

```
<400> SEQUENCE: 28

Thr Ile Tyr Tyr Ser Gly Asn Thr Tyr Tyr Asn Pro Ser Leu Lys Ser
1               5                   10                  15

<210> SEQ ID NO 29
<211> LENGTH: 11
<212> TYPE: PRT
<213> ORGANISM: Artificial Sequence
<220> FEATURE:
<223> OTHER INFORMATION: Hv CDR3 of HL161B or HL161BK

<400> SEQUENCE: 29

Arg Ala Gly Ile Leu Thr Gly Tyr Leu Asp Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Lv CDR1 of HL161B or HL161BK

<400> SEQUENCE: 30

Gly Gly Asn Asn Ile Gly Ser Lys Ser Val His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Lv CDR2 of HL161B or HL161BK

<400> SEQUENCE: 31

Asp Asp Ser Asp Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Lv CDR3 of HL161B or HL161BK

<400> SEQUENCE: 32

Gln Val Trp Asp Ser Ser Ser Asp His Val Val
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Hv CDR1 of HL161C

<400> SEQUENCE: 33

Gly Cys Tyr Met His
1               5

<210> SEQ ID NO 34
<211> LENGTH: 17
<212> TYPE: PRT
<213> ORGANISM: Artificial Sequence
<220> FEATURE:
<223> OTHER INFORMATION: Hv CDR2 of HL161C

<400> SEQUENCE: 34
```

Arg Ile Asn Pro Asn Ser Gly Gly Thr Asn Tyr Ala Gln Lys Phe Gln
1               5                   10                  15

Gly

<210> SEQ ID NO 35
<211> LENGTH: 9
<212> TYPE: PRT
<213> ORGANISM: Artificial Sequence
<220> FEATURE:
<223> OTHER INFORMATION: Hv CDR3 of HL161C

<400> SEQUENCE: 35

Asp Tyr Ser Gly Trp Ser Phe Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Lv CDR1 of HL161C

<400> SEQUENCE: 36

Arg Ala Ser Gln Gly Ile Ser Asn Tyr Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Lv CDR2 of HL161C

<400> SEQUENCE: 37

Ala Ala Ser Ser Leu Gln Ser
1               5

<210> SEQ ID NO 38
<211> LENGTH: 10
<212> TYPE: PRT
<213> ORGANISM: Artificial Sequence
<220> FEATURE:
<223> OTHER INFORMATION: Lv CDR3 of HL161C

<400> SEQUENCE: 38

Gln Gln Tyr Asp Ser Tyr Pro Pro Thr Phe
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Hv CDR1 of HL161D

<400> SEQUENCE: 39

Ser Tyr Tyr Trp Gly
1               5

<210> SEQ ID NO 40
<211> LENGTH: 16
<212> TYPE: PRT
<213> ORGANISM: Artificial Sequence
<220> FEATURE:
<223> OTHER INFORMATION: Hv CDR2 of HL161D

```
<400> SEQUENCE: 40

Asn Ile Tyr Tyr Ser Gly Ser Thr Tyr Tyr Asn Pro Ser Leu Met Ser
1               5                   10                  15

<210> SEQ ID NO 41
<211> LENGTH: 13
<212> TYPE: PRT
<213> ORGANISM: Artificial Sequence
<220> FEATURE:
<223> OTHER INFORMATION: Hv CDR3 of HL161D

<400> SEQUENCE: 41

Gln Leu Ser Tyr Asn Trp Asn Asp Arg Leu Phe Asp Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Lv CDR1 of HL161D

<400> SEQUENCE: 42

Gly Gly Asn Asn Ile Gly Ser Lys Asn Val His
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Lv CDR2 of HL161D

<400> SEQUENCE: 43

Arg Asp Ser Asn Arg Pro Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Lv CDR3 of HL161D

<400> SEQUENCE: 44

Gln Val Trp Asp Ser Ser Thr Val Val
1               5
```